United States Patent [19]

Ohsawa

[11] Patent Number: 4,905,668
[45] Date of Patent: Mar. 6, 1990

[54] ENDOSCOPE APPARATUS

[75] Inventor: Akira Ohsawa, Yokohama, Japan

[73] Assignee: Olympus Optical Co., Ltd., Tokyo, Japan

[21] Appl. No.: 325,835

[22] Filed: Mar. 20, 1989

[30] Foreign Application Priority Data

| May 16, 1988 | [JP] | Japan | 63-120045 |
| Feb. 6, 1989 | [JP] | Japan | 64-28077 |
| Feb. 6, 1989 | [JP] | Japan | 64-28076 |

[51] Int. Cl.⁴ ............................................. A61B 1/04
[52] U.S. Cl. ......................................... 128/6; 358/98
[58] Field of Search ..................... 128/4, 6; 358/98

[56] References Cited

U.S. PATENT DOCUMENTS

| 4,157,216 | 6/1979 | Plummer | 128/6 X |
| 4,196,990 | 4/1980 | Forsyth | 128/6 X |
| 4,478,212 | 10/1984 | Asano | 128/6 |
| 4,480,636 | 11/1984 | Karaki et al. | 128/6 |
| 4,682,586 | 7/1987 | Matsuo | 128/6 |
| 4,846,155 | 7/1989 | Kimura | 128/6 |

FOREIGN PATENT DOCUMENTS

| 57-148928 | 9/1982 | Japan . |
| 59-129822 | 7/1984 | Japan . |
| 59-137921 | 8/1984 | Japan . |
| 60-11316 | 1/1985 | Japan . |
| 60-217783 | 10/1985 | Japan . |
| 61-2120 | 1/1986 | Japan . |
| 61-179129 | 8/1986 | Japan . |
| 62-14412 | 1/1987 | Japan . |
| 62-84735 | 4/1987 | Japan . |
| 63-271217 | 11/1988 | Japan . |

Primary Examiner—William H. Grieb
Attorney, Agent, or Firm—Armstrong, Nikaido, Marmelstein, Kubovcik & Murray

[57] ABSTRACT

This endoscope apparatus comprises an endoscope body having an image transmitting member transmitting an image formed by an image forming optical system to the rear end side of an insertable part, an image receiving apparatus removably connected with the endoscope body and receiving the image transmitted by the image transmitting member and a focus adjusting apparatus which is provided in the image receiving apparatus and by which the focus of the image emitted from the exit end of the image transmitting member and formed for the image receiving apparatus can be adjusted and is further provided with a detecting apparatus detecting such reference position on the endoscope body side as the exit end surface position of the image transmitting member and a detecting apparatus detecting the kind of the endoscope body.

41 Claims, 20 Drawing Sheets

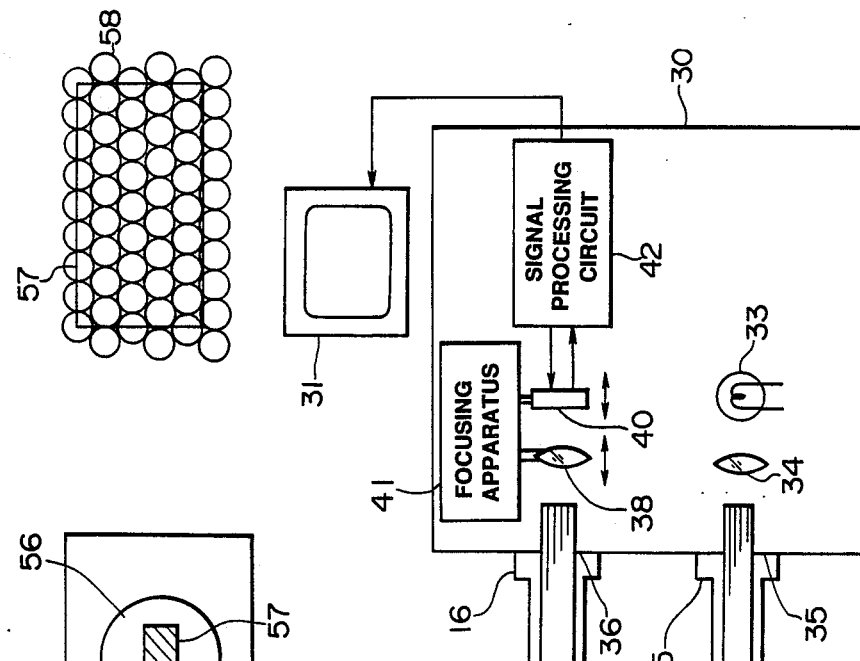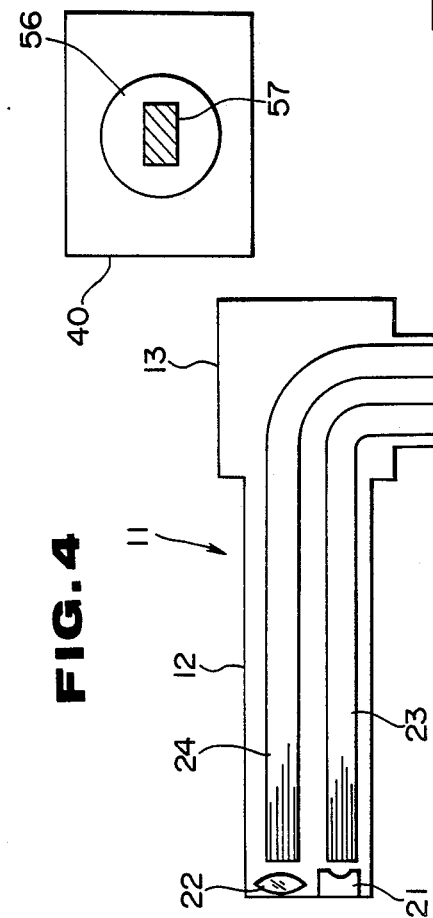

ENDOSCOPE APPARATUS

FIELD OF THE INVENTION

This invention relates to an endoscope apparatus wherein an endoscope image transmitted by such image transmitting means as an image guide is received by such image receiving means as a solid state imaging device or still camera.

RELATED ART STATEMENT

Recently, there is extensively utilized an endoscope whereby organs within a body cavity can be observed by inserting an elongate insertable part into the body cavity or, as required, various therapeutic treatments can be made by using treating instruments inserted through a treating instrument channel.

There are also suggested various electronic endoscopes using such solid state imaging device as a charge coupled device (CCD) for an image receiving means. By using such electronic endoscope, an endoscope receiving image can be observed with a television monitor.

Apart from such electronic endoscope, there is considered a method of observing an endoscope image with a television monitor wherein a solid state imaging device is provided on the exit end side of an image guide in such endoscope as a fiber scope and an image guide image is received by this solid state imaging device. Two examples of this method shall be explained respectively by using FIGS. 35 and 36.

In the first example, as shown in FIG. 35, an externally fitted television camera 5 having a solid state imaging device 6 is connected to an eyepiece part 2 of an endoscope (fiber scope) 1. An image guide 3 consisting of a fiber bundle is inserted through the above mentioned endoscope 1 and the rear end surface of this image guide 3 is opposed to an eyepiece lens 4 provided within the above mentioned eyepiece part 2. The above mentioned television camera 5 has an image forming lens 7 opposed to the above mentioned eyepiece lens 4 and the above mentioned solid state imaging device 6 is arranged in the image forming position of the image forming lens 7. This example is shown, for example, in the publication of Japanese Patent Application Laid Open No. 217783/1985. In such example, the focus of the image guide image is adjusted by the mechanical precision between the eyepiece part 2 and television camera 5.

In the second example, as shown in FIG. 36, an image forming lens 8 and solid state imaging device 6 are fixed within an endoscope light source apparatus or signal processing apparatus (video processor) and an image guide 3 is connected to this light source apparatus or signal processing apparatus through an inserting adapter so that the image of the end surface of this image guide 3 may be formed on the solid state imaging device 6 by the image forming lens 8. This example is shown, for example, in the publication of Japanese Patent Application Laid Open No. 148928/1982.

However in the first example, there are problems that the eyepiece part 2 and television camera 5 high in the fitting precision must be used, are complicated in the structure, are expensive and may be difficult to make in some case.

In the second example, the solid state imaging device 6 and image guide 3 can not be positioned at a high precision and the image is likely to be defocused.

These problems are also the same in the case of photographing an endoscope image with a still camera using a silver salt film or the like.

Thus, so far, the image guide and image receiving means have been set in primary positions by a mechanical methanism so that an image guide image may be formed on the imaging means. However, in the endoscope, depending on its kind, the position of the image surface of the image guide may be different. Therefore, image receiving means exclusively for the respective endoscopes have had to be prepared.

Also, an endoscope apparatus provided with a means of varying the projecting magnification or slipping the image forming position within an adapter connecting the eyepiece part of the fiber scope and the photographing apparatus with each other in order to prevent the generation of moire stripes is disclosed in the publication of each of Japanese Patent Application Laid Open Nos. 129822/1984 and 137921/1984. An adapter connecting the eyepiece part of the endoscope and the photographing apparatus with each other and adjusting the focus is disclosed in the publication of the Japanese Utility Model Application No. 11316/1985. An adapter connecting the eyepiece part of the fiber scope and the photographing apparatus with each other and set to be focused at the time of connecting them is disclosed in the publication of Japanese Utility Model Laid Open No. 14412/1987. However, in case the focus is adjusted by the adapter, the formation will become complicated, connecting places will become many, the operation will be complicated and the precision will reduce.

OBJECTS AND SUMMARY OF THE INVENTION

An object of the present invention is to provide an endoscope apparatus wherein an endoscope image transmitted by an image transmitting means can be received and the focus can be easily adjusted at a high precision.

Another object of the present invention is to provide an endoscope apparatus wherein, irrespective of the kind of the endoscope, the focus can be adjusted at a high precision.

Further another object of the present invention is to provide an endoscope apparatus wherein, irrespective of the kind of the endoscope, the endoscope image transmitted by an image transmitting means can be positively formed on an imaging receiving means.

The endoscope apparatus of the present invention comprises an endoscope body having an image transmitting means transmitting an image formed by an image forming optical system to the rear end side of an insertable part, an image receiving means removably connected with the above mentioned endoscope body and receiving the image transmitted by the above mentioned image transmitting means and a focus adjusting means provided in the above mentioned image receiving means and capable of adjusting the focus of the image emitted from the exit end of the above mentioned image transmitting means and formed on the above mentioned imaging receiving means. This endoscope apparatus is further provided with a detecting means detecting such reference position on the endoscope body side as the exit end surface position of the above mentioned image transmitting means to adjust the focus and a detecting means detecting the kind of the endoscope body.

BRIEF DESCRIPTION OF THE DRAWINGS

FIGS. 1 to 4 relate to the first embodiment of the present invention.

FIG. 1 is an explanatory view showing an essential part of an endoscope apparatus.

FIG. 2 is an explanatory view showing an image guide image formed on a solid state imaging device.

FIG. 3 is an explanatory view showing a range finding range within an image guide image.

FIG. 4 is a explanatory view showing the formation of the whole of an endoscope apparatus.

FIG. 5 is an explanatory view showing an essential part of an endoscope apparatus.

FIG. 6 is an explanatory view showing a connecting part of an image guide in a modification of the second embodiment.

FIG. 9 is an explanatory view showing an essential part of an endoscope apparatus.

FIGS. 10 and 11 are explanatory views respectively showing an essential part of an endoscope apparatus as non-focused.

FIG. 13 is an explanatory view showing the formation of the whole of an endoscope apparatus.

FIG. 14 is an explanatory view showing an imaging means.

FIG. 22 is an explanatory view showing an essential part of an endoscope apparatus.

FIGS. 23 and 24 are explanatory views respectively showing the positions of a mouthpiece and photoreflector as non-focused.

FIG. 27 is an explanatory view showing the formation of the whole of an endoscope apparatus having a solid state imaging device as an imaging means.

FIG. 28 is an explanatory view showing an essential part of an endoscope apparatus having a silver salt film as an image receiving means.

FIG. 29 is an explanatory view showing the formation of a focus adjusting means.

FIGS. 30 to 32 are explanatory views respectively showing the formation of a detecting means.

FIG. 33 is an explanatory view showing an essential part of an endoscope apparatus having a solid state imaging device as an image receiving means.

FIG. 34 is an explanatory view showing an essential part of an endoscope apparatus having a silver salt film as an image receiving means.

FIG. 35 is an explanatory view showing an example of a means of imaging an image guide image with a solid state imaging device.

FIG. 36 is an explanatory view showing another example of a means of imaging an image guide image with a solid state imaging device.

DETAILED DESCRIPTION OF PREFERRED EMBODIMENTS

Figure 1:
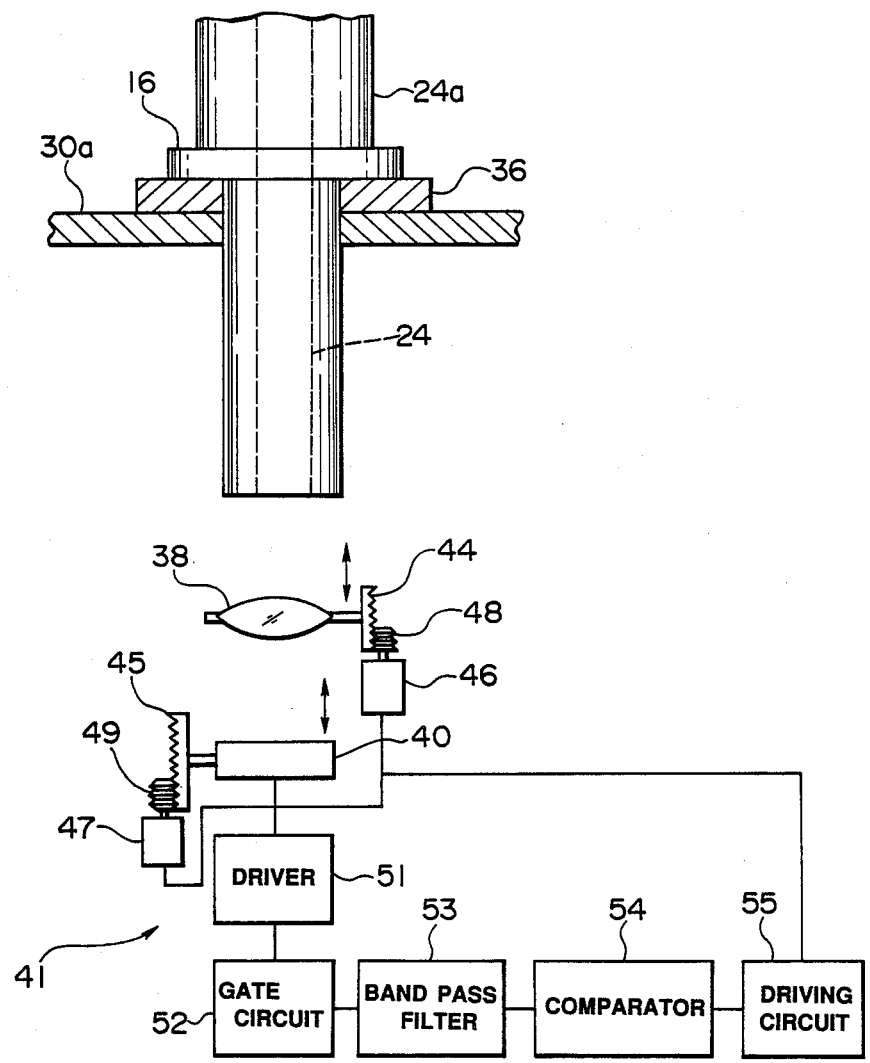

The first embodiment of the present invention is shown in FIGS. 1 to 4.

As shown in FIG. 4, an endoscope apparatus is provided with an endoscope 11, a video processor 30 to which this endoscope 11 is connected and a monitor 31 connected to this video processor.

The above mentioned endoscope 11 comprises an elongate and, for example, flexible insertable part 12, a thick operating part 13 connected to this insertable part 12 at the rear end and a flexible universal cord 14 extended from the side of this operating part 13. The above mentioned universal cord 14 is branched on the tip side into two branches, one branch is provided in the tip part with a light guide connector 15 and the other branch is provided in the tip part with an image guide connector 16. A light distributing lens 21 and objective lens system 22 are arranged in the tip part of the above mentioned insertable part 12. A light guide 23 consisting of a fiber bundle is provided on the rear end side of the above mentioned light distributing lens 21. This light guide 23 is inserted through the above mentioned insertable part 12, operating part 13 and universal cord 14 and is connected in the base end part to the light guide connector 15. The tip surface of an image guide 24 as an image transmitting means consisting of a fiber bundle is arranged in the image forming position of the above mentioned objective lens system 22. This image guide 24 is inserted through the above mentioned insertable part 12, operating part 13 and universal cord 14 and is connected in the exit end part to the image guide connector 16.

On the other hand, the above mentioned video processor 30 is provided with a light guide connector receptacle 35 to which the light guide connector 15 of the above mentioned endoscope 11 is connected and an image guide connector receptacle 36 to which the image guide connector 16 is connected. A lamp 33 is provided within the above mentioned video processor 30 so that the light emitted from this lamp 33 may be condensed by a condenser lens 34 and may enter the entrance end of the light guide 23 of the light guide connector 15 connected to the above mentioned light guide connector receptacle 35.

An image forming lens 38 is arranged within the above mentioned video processor 30 so as to be opposed to the exit end surface of the image guide 24 of the image guide connector 16 connected to the above mentioned image guide connector receptacle 36. Such solid state imaging device 40 as a CCD as an image receiving means is arranged in the image forming position of this image forming lens 38. At least one of the above mentioned image forming lens 38 and solid state imaging device 40 is moved in the optical axial direction by a focusing apparatus 41 and is fixed in the optimum focal position. A signal processing circuit 42 is connected to the above mentioned solid state imaging device 40 so that the above mentioned solid state imaging device 40 may be driven by a driving signal from a driving circuit within the above mentioned signal processing circuit 42 and the signal read out may be processed to be a video signal by the above mentioned signal processing circuit 42. The video signal from the above mentioned signal processing circuit 42 is input into a monitor 31 in which the endoscope image is displayed.

The above mentioned focusing apparatus 41 is formed as shown in FIG. 1.

The image guide connector 16 to which the image guide 24 is fixed at the exit end is connected to the image guide connector reciptacle 35 provided on a sheath 30a of the video processor 30. By the way, the above mentioned image guide 24 is coated with an image guide sheath 24a.

The image forming lens 38 and solid state imaging device 40 arranged on the optical axis of the above mentioned image guide 24 are fitted respectively with racks 44 and 45 as moving means. Worms 48 and 49 fitted respectively to the driving shafts of motors 46 and 47 as driving devices are meshed with the respective racks 44 and 45 so that, when the respective motors 46 and 47 are rotated, the image forming lens 38 and solid state imaging device 40 may be moved in the optical axial direction.

The output signal of the solid state imaging device 40 is input into a driver 51 and the output of this driver 51 is input into a gate circuit 52. This gate circuit 52 limits the range finding range in the image on the end surface of the image guide 24 formed on the above mentioned solid state imaging device 40. The output of this gate circuit 52 is input into a band pass filter 53 extracting a specific frequency component corresponding to the pitch of the respective fiber element lines of the image guide 24 and the output of this band pass filter 53 is input into a comparator 54. The output of this comparator 54 is input into a driving circuit 55 rotating and driving the above mentioned motors 46 and 47. On the basis of the output of this driving circuit 55, at least one of the image forming lens 38 and solid state imaging device 40 is moved in the optical axial direction and is fixed in the optimum focal position.

The operation of this embodiment shall be explained with reference to FIGS. 2 and 3.

The light emitted from the lamp 33 within the video processor 30 enters the light guide 23 at the entrance end through the conderser lens 34, is emitted from the tip surface of this light guide 23 and is radiated to an object through the light distributing lens 21. The returning light from this object is made to form an image on the tip surface of the image guide 24 by the objective lens system 22. This objective image is transmitted to the exit end surface of the above mentioned image guide 24. The image on the exit end surface of this image guide 24 is formed on the solid state imaging device 40 by the image forming lens 38. The output signal of this solid state imaging device 40 is input into the gate circuit 52 through the driver 51. As shown in FIG. 2, this gate circuit 52 limits and sets a range finding range 57 within the whole image 56 in the image guide formed on the solid state imaging device 40. Now, the thickness of the respective fiber element lines forming the above mentioned image guide 24 is substantially constant and a network pattern is formed on the end surface of the image guide 24 by the arrangement of the respective fiber element lines. The thickness of the above mentioned respective fiber element lines is so considerably larger than one pixel of the solid state imaging element 40 that the video signal showing the edge of the respective fiber element lines of the image guide 24 will be limited within a narrow frequency range of low frequencies. Therefore, as shown in FIG. 3, the output signal of the above mentioned gate circuit 52 has a specific frequency component corresponding to the pitch of the respective fiber element line images 58 of the image guide 24 within the above mentioned range finding range 57. This specific frequency component is extracted by the band pass filter 53. That is to say, the network pattern which is an optical feature of the image guide end surface is extracted. The specific frequency component extracted by this band pass filter 53 is input into the comparator 54 and is compared with a predetermined value so that focusing may be judged. That is to say, the larger the above mentioned specific frequency component, the nearer the focusing. On the basis of the output of this comparator 54, at least one of the image forming lens 38 and solid state imaging device 40 will be moved in the optical axial direction through the driving circuit 55, motors 46 and 47, worms 48 and 49 and racks 44 and 45 and will be fixed in the optimum focal position.

Thus, in this embodiment, the end surface of the image guide 24 is detected from the output signal of the solid state imaging device 40 and at least one of the image forming lens 38 and solid state imaging device 40 is moved in the optical axial direction in response to the position of the end surface to automatically adjust the focus. Therefore, according to this embodiment, the focus can be easily adjusted at a high precision without requiring any minute manual adjustment and high mechanical precision.

As the focus is adjusted on the basis of the end surface position of the image guide 24, irrespective of the kind of the endoscope, the focus can be adjusted at a high precision.

Also, as described above, the thickness of the respectise fiber element lines forming the image guide is substantially constant and is so considerably larger than one pixel of the solid state imaging device 40 that the video signal of the edge of the image guide 24 will be limited within a narrow frequency range of low frequencies. Thereby, the image guide end surface image can be extracted with a circuit of a comparatively simple band pass filter or the like and the range can be easily found.

Generally, the thickness of the respective fiber element lines of the image guide 24 is different depending on the kind of the endoscope and the image guide image projected on the solid state imaging device 40 has a width more than three times as large in the spatial frequency. Thereby, when the band pass filter 53 having a pass band conformed to the spatial frequency by the the thickness of the fiber element lines of the respective endoscopes is used as switched, an accurate focusing will be able to be obtained. As the bundle diameter of the image guide 24 is also different depending on the endoscope, when the size of the range finding range 57 is conformed to the respective endoscopes by switching the gate time of the gate circuit 52, a more accurate focusing will be able to be obtained.

By the way, the focus may be adjusted by moving only one of the image forming lens 38 and solid state imaging device in the optical axial direction.

Figure 5:
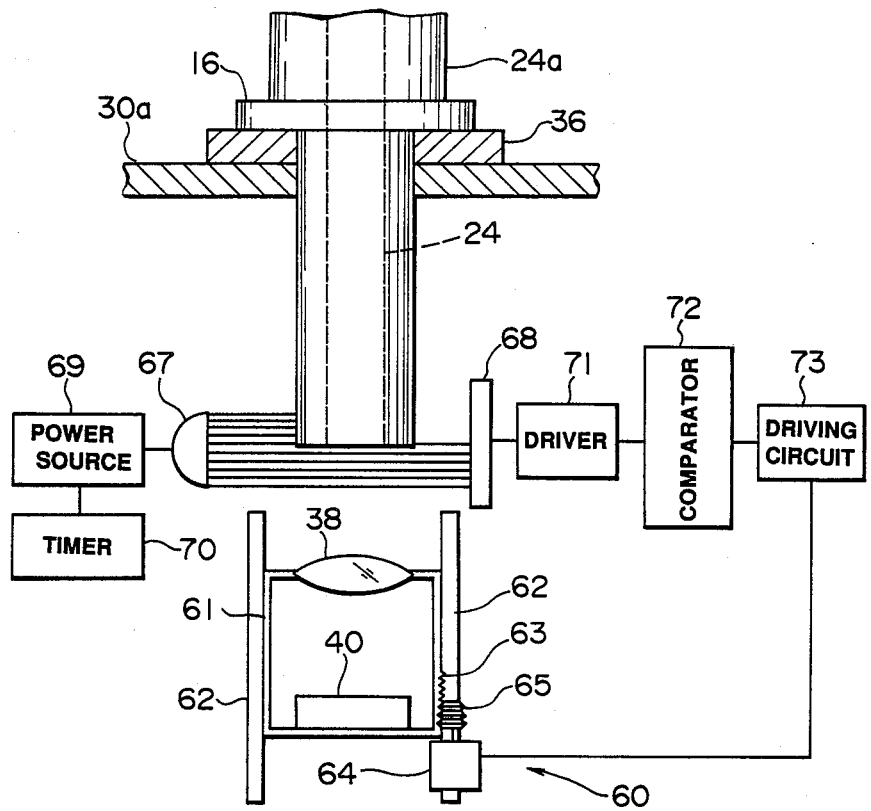
FIGS. 5 and 6 relate to the second embodiment of the present invention.
Figure 6:
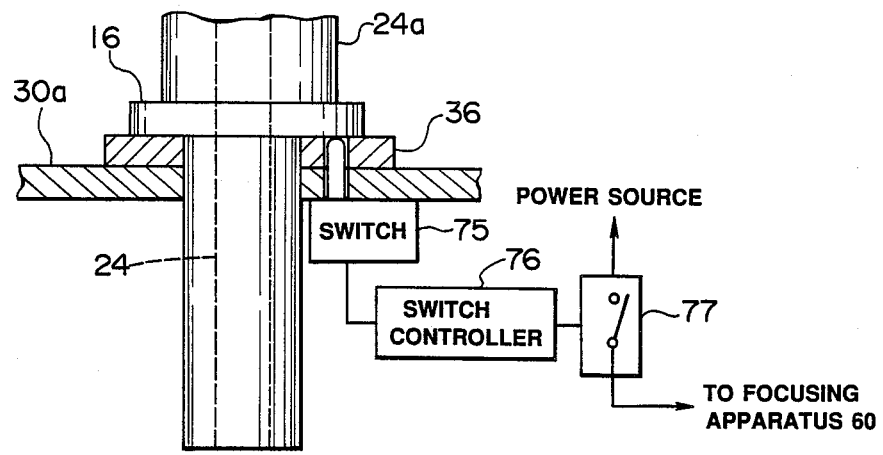

The second embodiment of the present invention is shown in FIGS. 5 and 6.

In a focusing apparatus 60 in this embodiment, the image forming lens 38 and solid state imaging device 40 are held by a lens housing 61 and their relative positions with each other are primarily determined. The above mentioned lens housing 61 can be moved in the optical axial direction along rails 62. A rack 63 as a moving means is fitted to the side of the above mentioned lens housing 61. A worm 65 fitted to the driving shaft of a motor 64 as a driving apparatus is meshed with this rack 63. By rotating the motor 64, the image forming lens 38 and solid state imaging device 40 together with the lens housing 61 can be moved in the optical axial direction.

Within the video processor 2, on the side of the exit end part of the image guide 24 connected to the image guide connector receptacle 36, a light projecting apparatus 67 and light receiving device 68 are arranged with the exit end part of this image guide 24 between them. The light emitted from the above mentioned light projecting apparatus 67 crosses the exit end part of the image guide 24, is partly intercepted by this exit end part and reaches the light receiving device 68. The above mentioned light projecting apparatus 67 is driven by a power source 69 which is controlled to be on/off by a timer 70. The above mentioned light receiving device 68 is such position detecting device as a line sensor. The output of this light receiving device 67 is input into a comparator 72 through a driver 71 and the output of this comparator 72 is input into a driving circuit 73 driving the above mentioned motor 64.

The other formations are the same as in the first embodiment.

The operation of this embodiment shall be explained in the following.

When the exit end part of the image guide 24 crosses the light emitted from the light projecting apparatus 67, the position of the exit end part of the image guide 24 will be detected. This detecting output of the light receiving device 68 is compared with a predetermined value in the comparator 72 and a signal corresponding to the difference between this value and the detecting output of the light receiving device 68 is input into the driving circuit 73. This driving circuit 73 drives the motor 64 on the basis of the signal from the above mentioned comparator 72. Thereby, the lens housing 61 will be moved to position in which the image guide image projected on the solid state imaging device 40 by the image forming lens 38 is focused.

By the way, the light emitted from the light projecting apparatus 67 may cause fogging and therefore will be automatically extinguished by the timer 70 when a predetermined time has elapsed.

Thus, according to this embodiment, as the lens housing 61 is moved by only the position signal from the light receiving device 68, the circuit formation is simple.

The other formations and effects are the same as in the first embodiment.

In the modification shown in FIG. 6, the image guide connector receptacle 36 of the video processor 30 is provided with such switch 75 as a push-button switch which will be on only hen the image guide connector 16 is connected. Also, a switch 77 is provided in the power source feeding path to the above mentioned focusing apparatus 60 so that the output of the above mentioned switch 75 may be input into a switch controller 76 controlling the above mentioned switch 77 to be on/off. When the above mentioned switch 75 is on, the switch 77 will be switched on (closed) by the switch controller 76 and, when the above mentioned switch 75 is off, the switch 77 will be switched off (opened). Therefore, according to this modification, only when the image guide 24 is connected, the power source of the focusing apparatus will be on.

Figure 7:
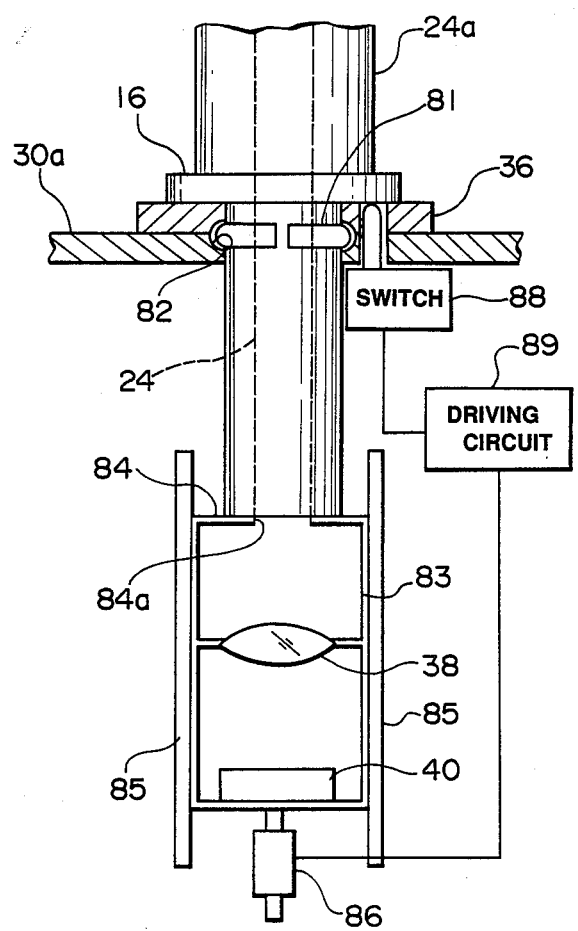
FIG. 7 is an explanatory view showing an essential part of an endoscope apparatus of the third embodiment of the present invention.

The third embodiment of the present invention is shown in FIG. 7.

In this embodiment, such fixing member 81 as a C-ring is fitted to the outer periphery of the exit end part of the image guide 24. On the other hand, a recess 82 into which the above mentioned fixing member 81 is fitted is formed in the image guide connector receptacle 36 into which the exit end part of the above mentioned image guide 24 is inserted. Therefore, when the above mentioned image guide 24 exit end part is inserted into the image guide connector receptacle 36, it will be fixed by the fitting of the above mentioned fixing member 81 and recess 82 and will not be pulled out unless a force larger than is predetermined is applied.

The image forming lens 38 and solid state imaging device 40 are held by an optical system housing 83 and their relative positions with each other are primarily determined. The image guide 24 side end part 84 of the above mentioned optical system housing 83 contacts the exit end surface of the above mentioned image guide 24 and an opening 84a passing the light from the image guide 24 is formed in this end part 84. By the way, the positions of the above mentioned image forming lens 38, solid state imaging device 40 and end part 84 are set in such positions that, when the image guide 24 exit end surface is in close contact with the above mentioned end part 84, the image guide image projected on the solid state imaging device may be focused. The above mentioned optical system housing 83 can be moved in the optical axial direction along rails 85 by such moving means 86 as a solenoid.

Further, there is provided such switch 88 as a push-button switch which will be on only when the image guide connector 16 is connected to the image guide connector receptacle 36. The output of this switch 88 is input into a driving circuit 89 driving the above mentioned moving means 86. In case the above mentioned switch 88 is closed, this driving circuit 89 will drive the moving means 86 to move the above mentioned optical system housing 83 to the image guide 24 exit end part side.

In this embodiment, when the image guide 24 is inserted into the image guide connector receptacle 36, the switch 88 will close and the optical system housing 83 will be moved to the image guide 24 exit end part side by the moving means 86. Thereby, the image guide 24 exit end surface will be in close contact with the end part 84 having the opening 84a of the optical system housing 83, the positions of the image guide 24 exit end surface, image forming lens 38 and solid state imaging device 40 will be determined so that the image guide image projected on the solid state imaging device 40 by the image forming lens 38 may be focused and the image guide image will be formed on the solid state imaging device 40.

Thus, according to this embodiment, a detector or the like detecting the position of the exit end surface of the image guide 24 is not required and, with a simple structure, the focus is automatically adjusted so that the image guide image projected on the solid state imaging device 40 may be focused.

The other formations, operations and effects are the same as in the first embodiment.

Figure 8:
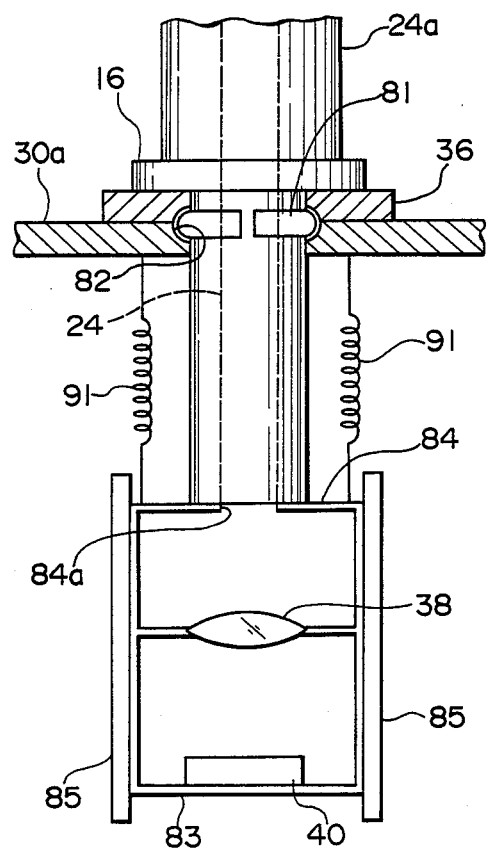
FIG. 8 is an explanatory view showing an essential part of an endoscope apparatus of the fourth embodiment of the present invention.

The fourth embodiment of the present invention is shown in FIG. 8.

In this embodiment, the same as in the third embodiment, such fixing member 81 as a C-ring is fitted to the outer periphery of the image guide 24 exit end part and a recess 82 in which the above mentioned fixing member 81 is fitted is formed in the image guide connector receptacle 36 in which this image guide 24 exit end part is inserted. The image forming lens 38 and solid state imaging device 40 are held by the optical system housing 83 and their relative positions with each other are primarily determined. The end part 84 on the image guide 24 side of the above mentioned optical system housing 83 contacts the exit end surface of the above mentioned image guide 24. An opening 84a passing the light from the image guide 24 is formed in this end part 84. The above mentioned optical system housing 83 can be moved in the optical axial direction along rails 85. The above mentioned optical system housing 83 is connected to the sheath 30a by such resilient members 91 as springs and is energized to the image guide 24 exit end side by these resilient members 91.

In this embodiment, when the image guide 24 is inserted into the image guide connector receptacle 36, the image guide 24 exit end surface will closely contact the end part 84 having the opening 84a of the optical system housing 83, the relative positions of the image guide 24 exit end surface, image forming lens 38 and solid state imaging device 40 will be determined so that the image guide image projected on the solid state imaging device 40 by the image forming lens 38 may be focused and the image guide image will be formed on the solid state imaging device 40.

Thus, according to this embodiment, any detector or the like detecting the position of the exit end surface of the image guide 24 is not required and, with a simpler structure than in the third embodiment, the focus is automatically adjusted so that the image guide image projected on the solid state imaging device 40 may be focused.

The other formations, operations and effects are the same as in the first embodiment.

Figure 9:
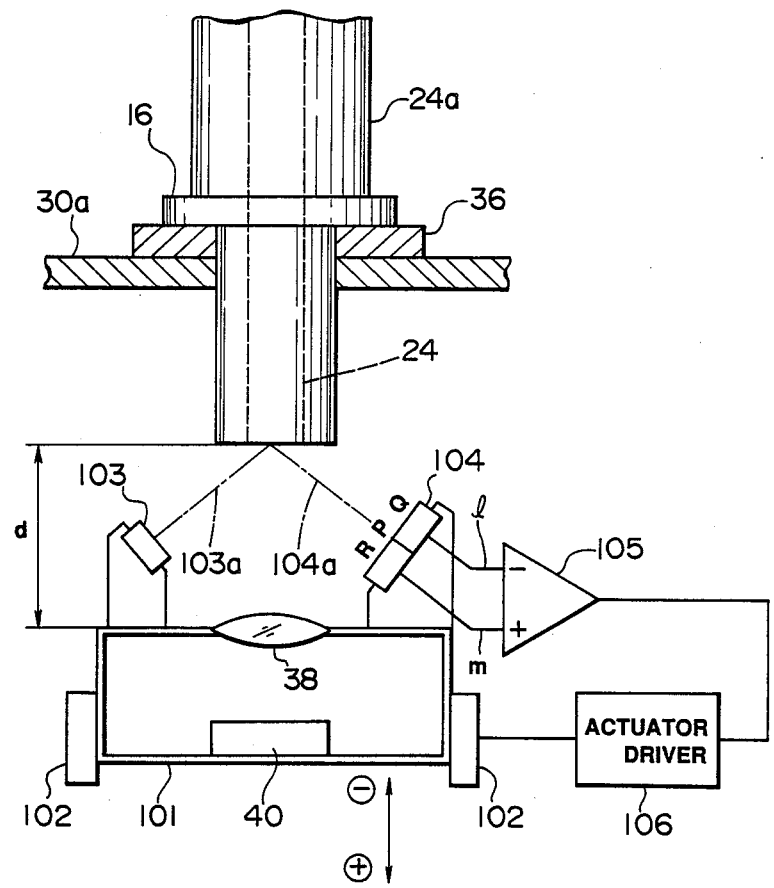
FIGS. 9 to 11 relate to the fifth embodiment of the present invention.
Figure 10:
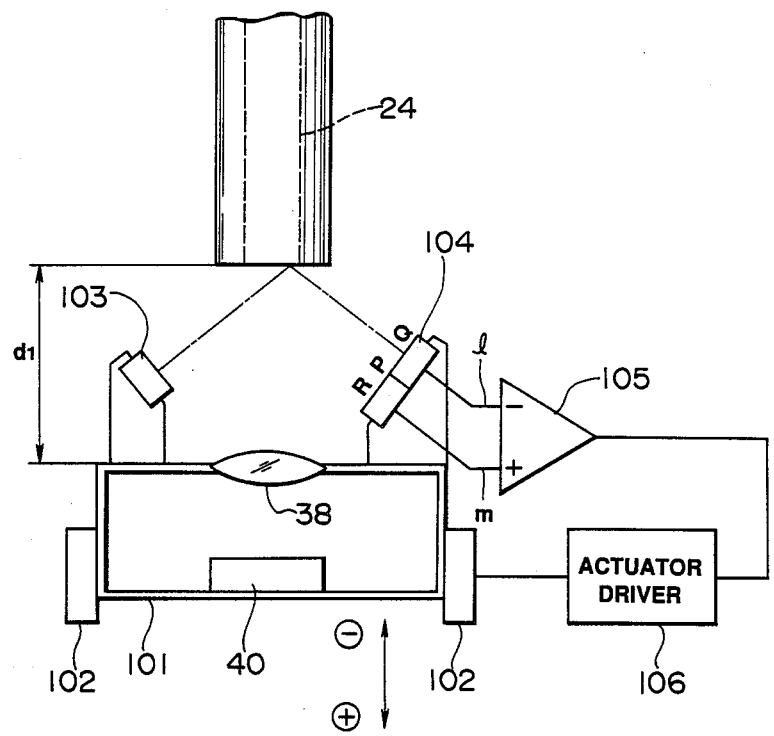
Figure 11:
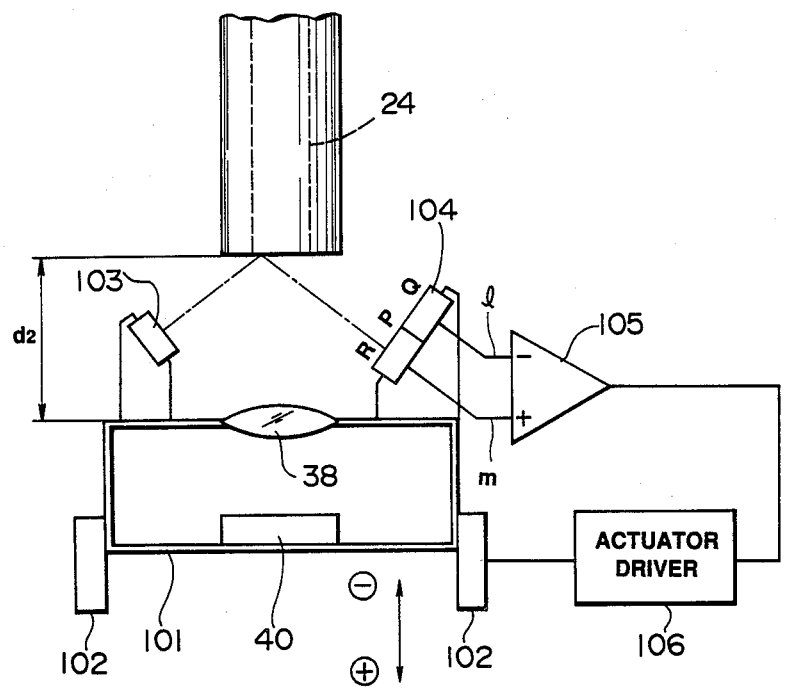

The fifth embodiment of the present invention is shown in FIGS. 9 to 11.

In this embodiment, an example of an automatic focusing apparatus using a triangle range finding method is shown as a means of detecting the position of the end surface of the image guide 24.

As shown in FIG. 9, the solid state imaging device 40 and image forming lens 38 are fixed to an optical housing 101 which can be moved in the optical axial direction of the imaging optical system by an actuator 102. A light projecting means 103 and light receiving means 104 are provided as a means of detecting the position of the end surface of the image guide 24, have their base line axes 103a and 104a directed in the optical axial direction of the image guide 24 and are fixed to the above mentioned optical housing 101 so as to have such angle that, when the image guide 24 is inserted, the light emitted from the light projecting means 103 will be reflected on the above mentioned image guide 24 end surface and will enter the light receiving means 104.

The output of the above mentioned light receiving means 104 is input into a differential amplifier 105 and, by the output of this differential amplifier 105, the above mentioned actuator 102 is driven with an actuator driver 106.

The other formations are the same as in the first embodiment.

The operation of this embodiment shall be explained in the following with reference to FIGS. 9 to 11.

In FIG. 9, when the image guide 24 is inserted into the image guide connector receptacle 36 and the distance between the end surface of the image guide 24 and the front end surface of the optical housing 101 is represented by d, the image guide 24 image will be formed as a focused image on the solid state imaging device 40. At this time, the emitted light from the light projecting means 103 will be reflected on the image guide 24 end surface and will be projected on the central position point P on the light receiving means 104. The sensor part of the above mentioned light receiving part 104 is formed of two divided sensors. The respective outputs of these sensors are input into the differential amplifier 105. In case the light is projected on the point P, the respective outputs l and m of the two divided sensors will be equal to each other, the output of the differential amplifier 105 will be zero and the output of the actuator driver 106 will stop the actuator 102.

Now, as shown in FIG. 10, when the end surface position of the image guide 24 is in the position of a distance $d_1$ ($d_1 > d$) from the front end surface of the optical housing 101, the emitted light of the light projecting means 103 will be reflected on the image guide 24 end surface and will be projected in the position of the point Q on the light receiving means 104. At this time, the outputs of the respective sensors of the light receiving means 104 will be $l > m$ and a negative output will be made from the differential amplifier 105. Receiving this output, the actuator driver 106 operates the actuator 102 and moves the optical housing 101 in the direction in the drawing. By this movement, the light projecting position on the light receiving means 104 is moved from the point Q to the point P side. When it reaches the point P, the output of the differential amplifier will become zero and the actuator 102 will stop.

Now, as shown in FIG. 11, when the end surface position of the image guide 24 is in the position of the distance $d_2$ ($d_2 < d$) from the front end surface of the optical housing 101, contrary to the case of FIG. 1, the emitted light of the light projecting means 103 will be projected in the position of the point R on the light receiving means 104. Thereby, the output of the light receiving means 104 will be m>1 and a positive output will be made from the differential amplifier 105. Thereby, the optical housing 101 moves in the + direction in the drawing and, when the light projecting position on the light receiving means 104 reaches the point P, the actuator 102 will stop.

Thus, according to this embodiment, by using the extensively known triangle range finding method, focusing can be easily obtained.

By the way, it is needless to say that not only the triangle range finding method but also any generally known automatic focusing apparatus can be used in the present invention.

By the way, when the image guide 24 image is formed on the solid state imaging device 40, a moire will be produced at the time of focusing. In all the embodiments of the present invention, if such optical low pass filter as a crystal filter is inserted in the optical axis of the imaging optical system at the time of focusing, the moire will be able to be extinguished. An example of applying a moire removing filter to the above mentioned fifth embodiment is shown in the following as the sixth embodiment of the present invention.

Figure 12:
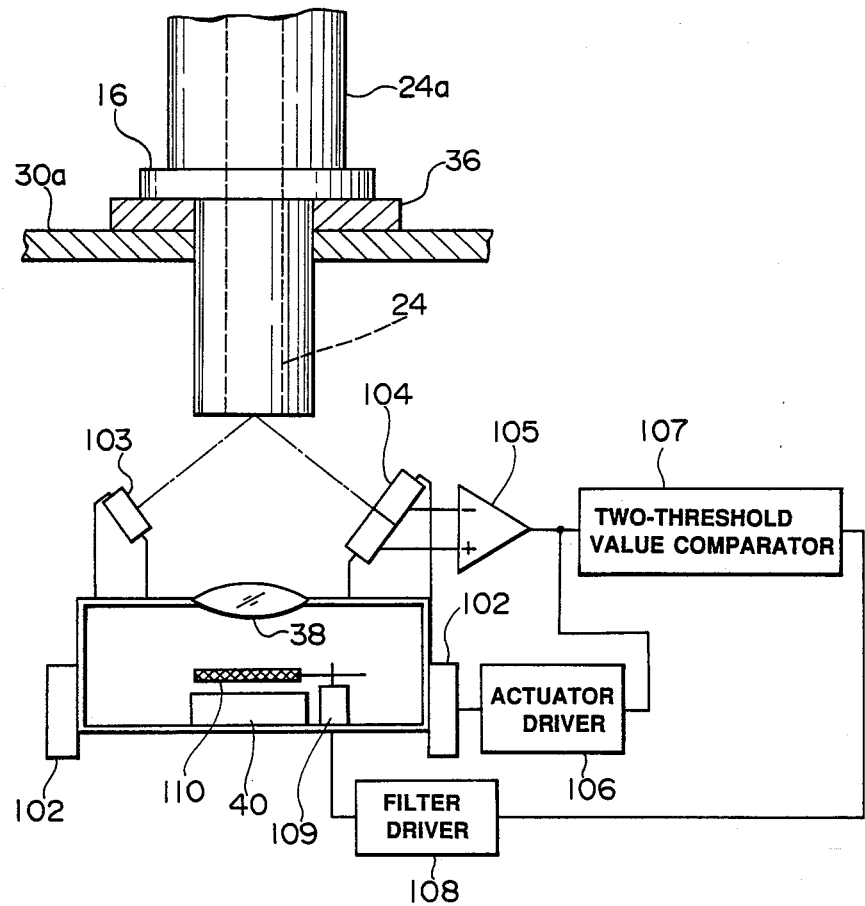
FIG. 12 is an explanatory view showing an essential part of an endoscope in the sixth embodiment of the present invention.

The sixth embodiment of the present invention is shown in FIG. 12.

In this embodiment, the output of the differential amplifier 105 is input into an actuator driver 106 and two-threshold value comparator 107. With the output of the above mentioned two-threshold value comparator 107, a filter driver 108 operates a filter actuator to insert or remove a crystal filter 110 into or from the optical axis of the imaging optical system. At the time of focusing, the output of the differential amplifier 105 will be of a value of zero or near zero but the output range at this time will be within a focusing range contained in the allowable turbulence circle of the lens system. When the output of this differential amplifier 105 enters the range of the upper limit value and lower limit value of the output at the time of focusing, a focusing signal will be output by the two-threshold value comparator 107 having the above mentioned upper limit value and lower limit value as reference voltages, the filter driver 108 will be in operation by this focusing signal and the crystal filter 110 will be inserted in the optical axis of the imaging optical system.

By the above operation, the moire at the time of focusing can be removed.

Also, by setting the optical positions of the image forming lens 38 and solid state imaging device 40 in the positions intentionally slightly slipped from the focusing position, the moire can be extinguished the same as in the above described case.

The other formations, operations and effects are the same as in the fifth embodiment.

Figure 13:
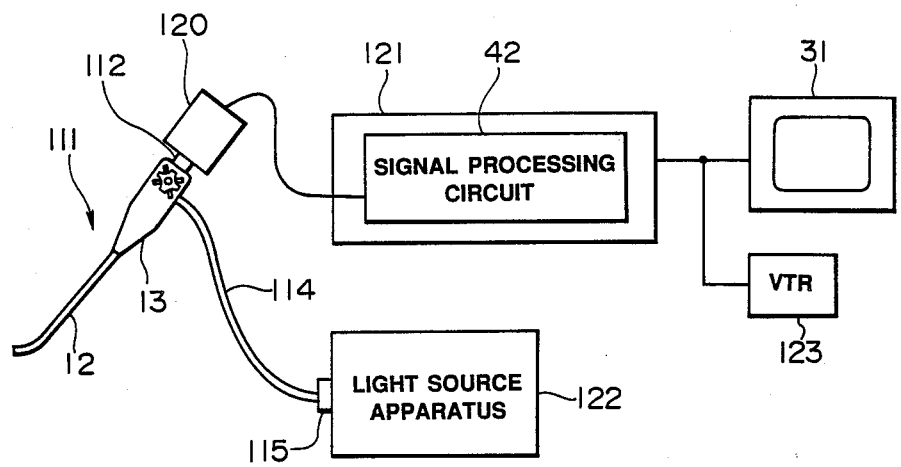
FIGS. 13 and 14 relate to the seventh embodiment of the present invention.
Figure 14:
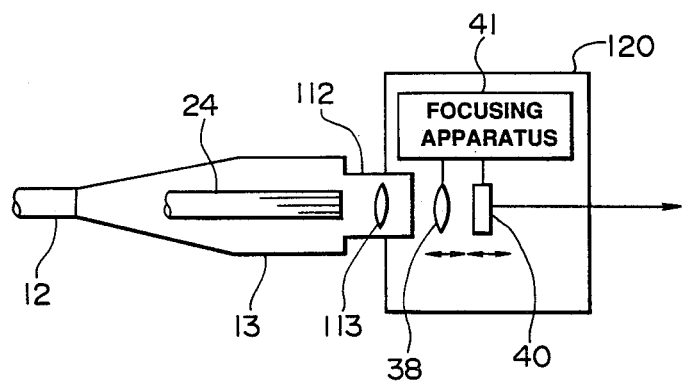

The seventh embodiment of the present invention is shown in FIGS. 13 and 14.

As shown in FIG. 13, an endoscope apparatus in this embodiment comprises an endoscope 111 whereby a naked eye observation is possible, a television camera 120 as a photographing means removably connected to the eyepiece part 112 of this endoscope 111, a signal processing apparatus 121 connected to the above mentioned television camera 120 and having a signal processing circuit 42, a monitor 31 connected to the above mentioned signal processing apparatus 121 and a light source apparatus 122 feeding an illuminating light to the above mentioned endoscope 111. Not only the above mentioned monitor 31 but also a VTR 123 and others can be connected to the above mentioned signal processing apparatus 121.

The above mentioned endoscope 111 comprises an elongate and, for example, flexible insertable part 12, a thick operating part 13 connected to this insertable part 12 at the rear end, the above mentioned eyepiece part 112 provided at the rear end of this operating part 13 and a flexible light guide cable 114 extended from the side of the above mentioned operating part 13. The above mentioned light guide cable 114 is provided in the end part with a light guide connector 115 connected to the above mentioned light source apparatus 122.

The same as in the endoscope 11 shown in FIG. 4, a light distributing lens 21 and an objective lens system 22 are arranged in the tip part of the above mentioned insertable part 12. A light guide 23 is provided on the rear end side of the above mentioned light distributing lens 21, is inserted through the above mentioned insertable part 12, operating part 13 and light guide cable 114 and is connected in the base end part to a light guide connector 115.

The tip surface of an image guide 24 as an image transmitting means consisting of a fiber bundle is arranged in the image forming position of the above mentioned objective lens system 22. This image guide 24 is inserted through the above mentioned insertable part 12 and operating part 13 and is opposed at the exit end to an eyepiece lens 113 within the above mentioned eyepiece part 112 as shown in FIG. 14. The object image formed by the above mentioned objective lens system 22 is transmitted to the eyepiece part 112 by the image guide 24 and can be observed with a naked eye from this eyepiece part 112.

As shown in FIG. 14, the above mentioned television camera 120 comprises a solid state imaging device 40 imaging the endoscope image, an image forming lens 38 forming the endoscope image on this solid state imaging device 40 and a focusing apparatus 41 focusing the endoscope image on the solid state imaging device 40 by moving in the optical axial direction at least one of the above mentioned image forming lens 38 and solid state imaging device 40.

In this embodiment, in case the television camera 120 is connected to the eyepiece part 112 of the endoscope 111, the endoscope image transmitted by the image guide 24 will be formed on the solid state imaging device 40 through the eyepiece lens 113 and image forming lens 38. The electric signal output from this solid state imaging device 40 is converted to a video signal by the signal processing circuit 42 and is output to the monitor 31 and VTR 123 and the endoscope image is displayed in the above mentioned monitor 31 or is recorded, for example, in the above mentioned VTR 123.

The above mentioned focusing apparatus 41 is of the same formation as, for example, of the first embodiment. By this focusing apparatus 41, the focus is adjusted in response to the position of the end surface of the image guide 24.

According to this embodiment, such photographing means as the television camera 120 can be easily connected with the endoscope eyepiece part 112 so far required of a high precision.

The other formations, operations and effects are the same as in the first embodiment.

Figure 15:
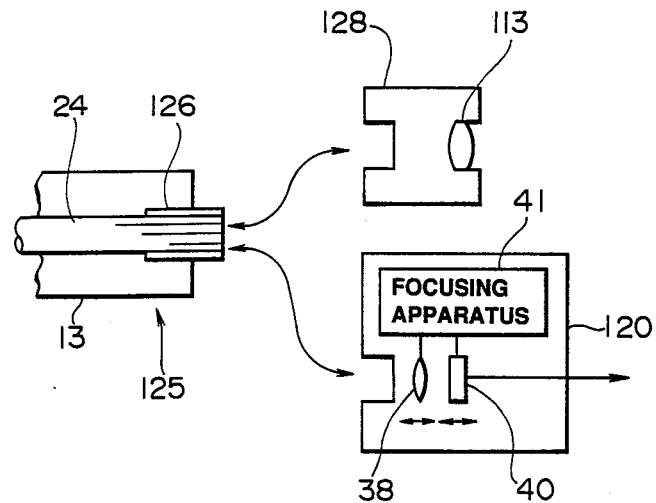
FIG. 15 is an explanatory view showing an essential part of an endoscope apparatus in the eighth embodiment of the present invention.

The eighth embodiment of the present invention is shown in FIG. 15.

The endoscope apparatus of this embodiment is provided with an endoscope body 125 of the formation of the endoscope 111 in the above mentioned seventh embodiment except the eyepiece part 112. In this endoscope body 125, the exit end part of the image guide 24 is led out of the rear end of the operating part 13. By the way, the exit end part of this image guide 24 is externally fitted with a mouthpiece 126.

An eyepiece unit 128 having the eyepiece lens 113 and the television camera 120 as a photographing means can be selectively connected to the rear end of the operating part 13 of the above mentioned endoscope body 125. When the eyepiece unit 128 is connected to the above mentioned operating part 13, the object image transmitted by the above mentioned image guide 24 will be able to be observed with a naked eye through the above mentioned eyepiece lens 113.

On the other hand, when the television camera 120 is connected to the above mentioned operating part 13, the image of the exit end surface of the above mentioned image guide 24 will be formed on the solid state imaging device 40 by the image forming lens 38 and will be imaged by this solid state imaging device 40. The output of this solid state imaging device 40 is converted to a video signal by the signal processing circuit 42 the same as in the seventh embodiment and is output to the monitor 31 and VTR 123. Also, by the focusing apparatus 41, the focus is adjusted in response to the position of the end surface of the image guide 24.

The other formations, operations and effects are the same as in the seventh embodiment. By the way, the focus adjusting means not only in the first embodiment but also in the second to fifth embodiments can be applied to this embodiment.

Figure 16:
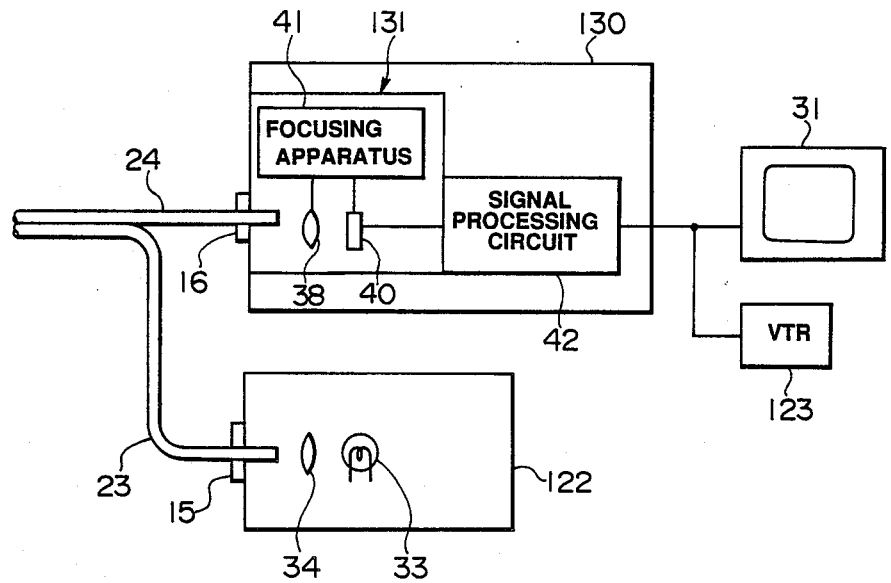
FIG. 16 is an explanatory view showing an essential part of an endoscope apparatus in the ninth embodiment of the present invention.

The ninth embodiment of the present invention is shown in FIG. 16.

This embodiment is of substantially the same formation as of the first embodiment but is provided with a separate signal processing apparatus 130 and light source apparatus 122. The above mentioned signal processing apparatus 130 is provided with an image receiving part 131 and signal processing circuit 42 and can be connected with the image guide connector 16 of the endoscope 11. The above mentioned image receiving part 131 comprises a solid state imaging device 40 imaging the endoscope image transmitted by the image guide 24, an image forming lens 38 forming the endoscope image on this solid state imaging device 40 and a focusing apparatus 41 focusing the endoscope image on the solid state imaging device 40 by moving in the optical axial direction at least one of the above mentioned image forming lens 38 and solid state imaging device 40. The output signal of the above mentioned solid state imaging device 40 is converted to a video signal by the signal processing circuit 42 and is output to the monitor 31 and VTR 123.

The above mentioned light source apparatus 122 is provided with a lamp 33 and condenser lens 34 and is to be connected with the light guide connector 15 of the endoscope 11.

According to this endoscope, the separate imaging means and signal processing circuit 42 connected by a cable as in the endoscope apparatus using an externally fitted conventional television camera are made integral so that the loss and noise caused by the cable may be reduced and a better image may be obtained.

The other formations, operations and effects are the same as in the first embodiment.

Figure 17:
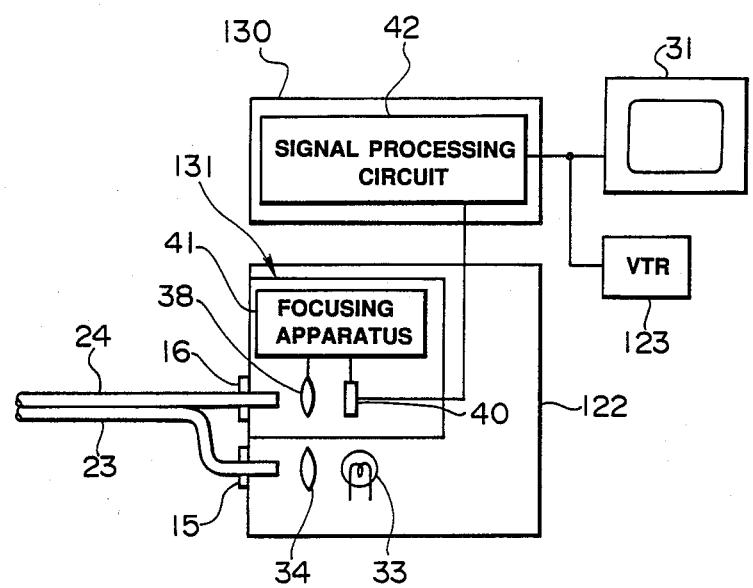
FIGS. 17 and 18 are explanatory views showing a modification of the ninth embodiment.
Figure 18:
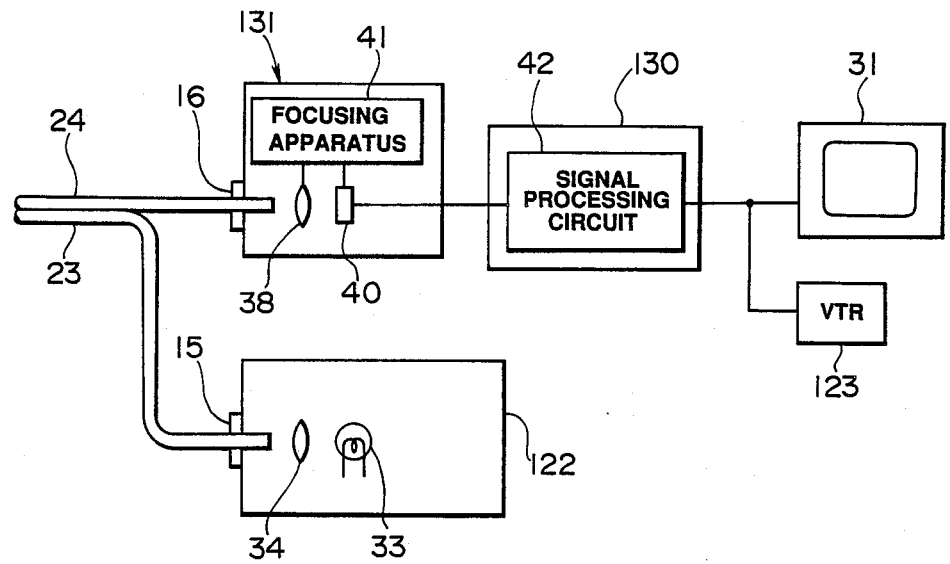

By the way, the formation of the imaging means, signal processing circuit and light source apparatus connected to the endoscope 11 is not limited to the formation shown in the first embodiment or ninth embodiment but may be the formation shown, for example, in FIG. 17 or 18.

In the endoscope apparatus shown in FIG. 17, an imaging part 131 is provided within the light source apparatus 122 and this light source apparatus 122 and a signal processing apparatus 130 having the signal processing circuit 42 are made separate.

In the endoscope apparatus shown in FIG. 18, the imaging part 131, light source apparatus 122 and signal processing apparatus 130 are all made separate.

Now, in the present invention, the photographing means may be a photographing still camera. It's example is shown as the following tenth embodiment.

Figure 19:
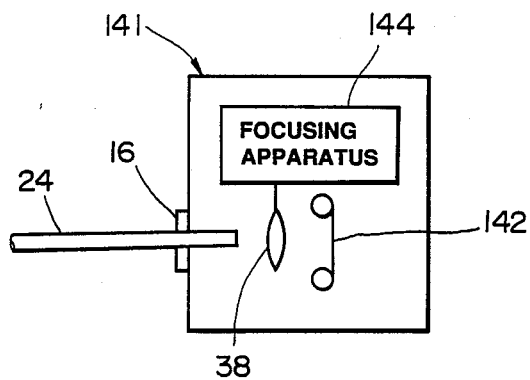
FIG. 19 is an explanatory view showing an essential part of an endoscope apparatus in the tenth embodiment of the present invention.

The tenth embodiment of the present invention is shown in FIG. 19.

In this embodiment, the image guide connector 16 is connected to a still camera 141 which is provided with an image forming lens 38, a film 142 recording as a photograph an endoscope image formed by this image forming lens 38 and a focusing apparatus 144 focusing on the above mentioned film 142 the endoscope image by moving in the optical axial direction the above mentioned image forming lens 38.

In this embodiment, the image on the exit end surface of the image guide 24 is formed on the film 142 by the image forming lens 38 and is recorded in this film. The focus is adjusted by the focusing apparatus 144 in response to the position of the end surface of the image guide 24.

By the way, the focus adjusting means to be used for the above mentioned focusing apparatus 144 may be the focus adjusting means in the second to fifth embodiments. As in the television camera 20 in the seventh and eighth embodiments, the still camera 14 may be connected to the eyepiece part 112 of the endoscope 111 or to the endoscope body 125 to replace the eyepiece unit 128.

The above mentioned still camera 141 can be connected to the endoscope or endoscope body by replacing the imaging means in the first to ninth embodiments.

Figure 20A:
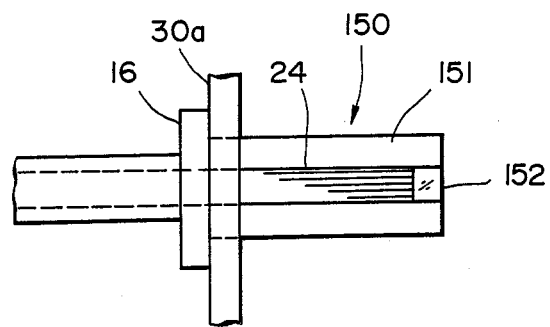
FIGS. 20(A) and (B) are explanatory views showing an image guide mouthpiece part of an endoscope.
Figure 20B:
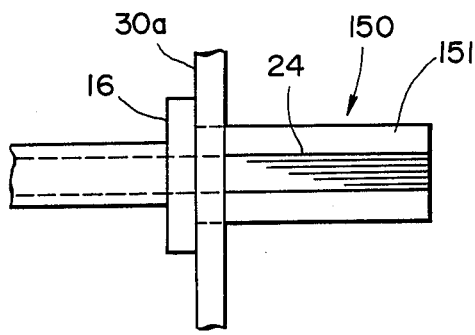

Now, as shown in FIGS. 20(A) and (B), the image guide mouthpiece part 150 in the image guide connector 16 of the endoscope connected to the photographing means is formed of the image guide 24 inserted through a mouthpiece 151 and may be provided in the tip part with a cover glass 152 protecting the image guide 24 as shown in FIG. 20(A), may have no cover glass as shown in FIG. 20(B) or may have a lens incorporated in the cover glass part. The positions of the mouthpiece end surface and image guide image surface may be different depending on the structure.

In such type as is shown in FIG. 20(B), the focus can be adjusted by detecting the position of the end surface of the mouthpiece 151 but, in such type as is shown in FIG. 20(B), if the focus is adjusted by detecting the position of the end surface of the mouthpiece 151, focusing will not be obtained. Therefore, in the following 11th to 13th embodiments, even with the type of FIG. 20(A), focusing will be obtained.

Figure 21:
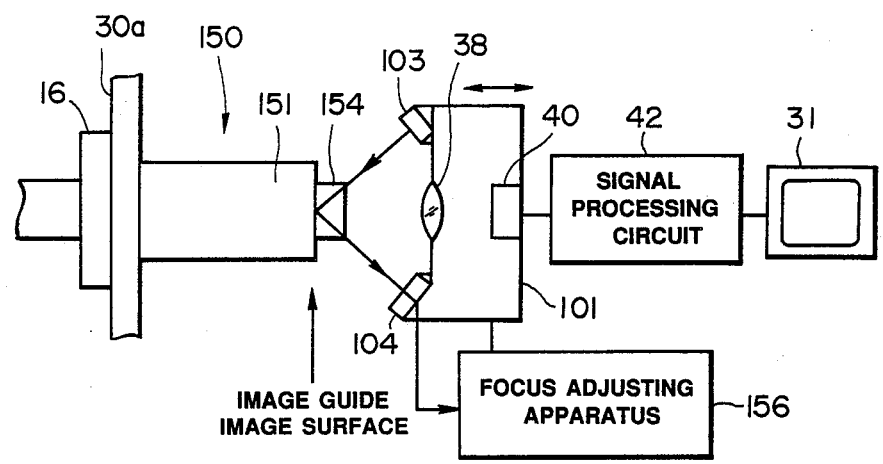
FIG. 21 is an explanatory view showing an essential part of an endoscope apparatus in the 11th embodiment of the present invention.
Figure 25:
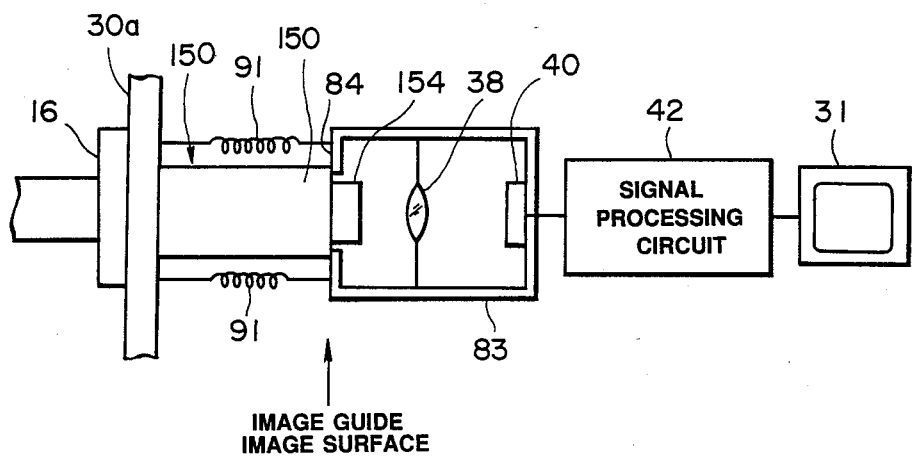
FIG. 25 is an explanatory view showing an essential part of an endoscope apparatus in the 13th embodiment of the present invention.

The 11th embodiment of the present invention is shown in FIG. 21.

In the image guide mouthpiece part 150 in this embodiment, an incision 154 is provided from the tip of this mouthpiece 151 to the position of the image guide image surface on the outer periphery of the mouthpiece 151 so that the surface in the position of the image guide image surface may be flat. The image forming lens 38 and solid state imaging device 40 are fixed to the optical housing 101. The light projecting means 103 and light receiving means 104 for the triangle range finding are arranged so as to be opposed to the rear end surface of the above mentioned incision 154 and are fitted to the above mentioned optical housing 101. The focus is automatically adjusted by moving the above mentioned optical housing 101 in the optical axial direction by a focus adjusting apparatus 156 on the basis of the output of the above mentioned light receiving means 104. By the way, the above mentioned focus adjusting apparatus 156 is formed of the differential amplifier 105, actuator driver 106 and actuator 102 in FIG. 9.

In this embodiment, the position of the rear end surface of the incision 154 provided in the mouthpiece 151 is detected by the triangle range finding to thereby detect the image guide image surface position and the focus is adjusted on the basis of this position.

The other formations, operations and effects are the same as in the fifth embodiment.

Figure 22:
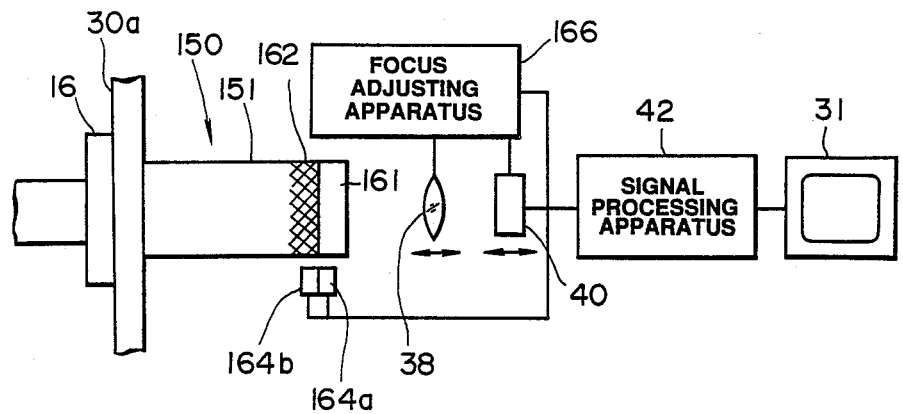
FIGS. 22 to 24 relate to the 12th embodiment of the present invention.
Figure 23:
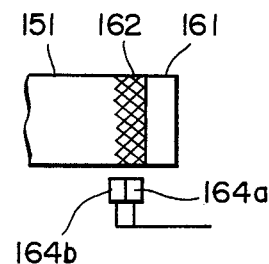
Figure 24:
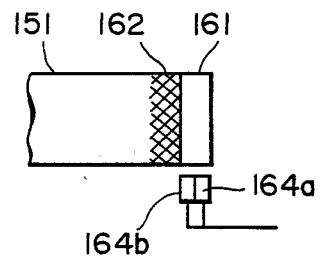

The 12th embodiment of the present invention is shown in FIGS. 22 to 24.

In the image guide mouthpiece part 150 in this embodiment, on the outer periphery of the mouthpiece 151, with the image guide image surface position as a boundary, a reflecting surface 161 is provided on the tip side and a non-reflecting surface 162 is provided on the base side. Near the image guide image surface position when the above mentioned image guide mouthpiece part 150 is inserted, two photoreflectors 164a and 164b are provided so as to be opposed to the above mentioned mouthpiece 151. By the way, the above mentioned photoreflectors 164a and 164b respectively receive the returning lights emitted and reflected by the mouthpiece 151 and will output an on-signal in case the received light amount is large but an off-signal in case the received light amount is small in response to the reflection factor of the mouthpiece 151.

Now, as shown in FIG. 22, the position of the image forming lens 38 or solid state imaging device 40 is set so that, when in focus, the photoreflector 164a will be on but the photoreflector 164b will be off. Then, as shown in FIG. 23, in case the image guide image surface is slipped near to the in-focus position, both photoreflectors 164a and 164b will be off and, as shown in FIG. 24, in case the image guide image surface is slipped far from the in-focus position, both photoreflectors 164a and 164b will be on. Thus, to which side of the in-focus position the image guide image surface is slipped can be judged. Focusing is obtained by moving at least one of the image forming lens 38 and solid state imaging device 40 with the focus adjusting apparatus 166 on the basis of this judging signal.

The other formations, operations and effects are the same as in the first embodiment.

In the image guide mouthpiece part 150 in this embodiment, the same as in the 11th embodiment, on the outer periphery of the mouthpiece 151, an incision 154 is provided from the mouthpiece 151 tip to the image guide image surface position so that the surface in the image guide image surface position may be flat. The image forming lens 38 and solid state imaging device 40 are fixed to the same optical system housing 83 as is shown in FIG. 8. This optical system housing 83 is connected to the sheath 30 by such resilient members 91 as springs and is energized to the image guide mouthpiece part 150 side by these resilient members 91. The end part 84 of the above mentioned optical system housing 83 contacts the rear end surface of the above mentioned incision 154.

In this embodiment, when the end part 84 of the optical system housing 83 contacts the rear end surface of the incision 154, an in-focus state will be made.

The other formations, operations and effects are the same as in the fourth embodiment.

Thus, according to the 11th to 13th embodiments, the focus is adjusted with the image guide image surface position as a reference position and therefore, even if the mouthpiece 151 end surface of the image guide mouthpiece part 150 and the image guide image surface are different depending on the endoscope, the focusing will be able to be made.

By the way, in the first to 13th embodiments, the focus may be adjusted by moving in the optical axial direction the image guide connector receptacle provided on the photographing means side and moving the image guide image surface position in the optical axial direction.

The image transmitting means is not limited to the image guide consisting of a fiber bundle but may be a self-convergent photoconductor (Trade name: Selfox) or a relay lens. The respective embodiments except the first embodiment can be applied to forming an image on the exit end surface with the above mentioned self-convergent photoconductor. In the self-convergent photoconductor or relay lens in which the exit end surface position and the image forming position are different, as in the 11th to 13th embodiments, the focus can be adjusted by providing a reference position conformed to the image forming position.

The present invention is not limited to the automatic focus adjustment. For example, the focus may be manually adjusted by the user on the basis of the information of a reference position detected on the endoscope body side.

As explained above, according to the first to 13th embodiments, the imaging means removably connected to the endoscope body is provided with a focus adjusting means and therefore there are such effects that the endoscope image transmitted by the image transmitting means can be received and the focus can be easily adjusted at a high precision.

The 14th and 15th embodiments of the present invention shall be schematically explained in the following with reference to FIG. 26.

This endoscope apparatus comprises an endoscope body 202 having an image transmitting means 201 transmitting an endoscope image and an image receiving means 203 removably connected with the above mentioned endoscope body 202 and receiving the endoscope image transmitted by the above mentioned image transmitting means 201 and is provided with a detecting means 204 detecting the kind of the above mentioned endoscope body 202 and a focus adjusting means 205 capable of adjusting the focus of an image emitted from the exit end of the above mentioned image transmitting means 201 and formed for the above mentioned photographing means 204 on the basis of the image surface position of the above mentioned image transmitting means 201 corresponding to the kind of the endoscope body 202 detected by the above mentioned detecting means 204. The above mentioned image receiving means 203 has, for example, an image forming lens 206 and a solid state imaging device or silver salt film 207 receiving the endoscope image formed by this image forming lens 206.

In this endoscope apparatus, the kind of the endoscope body 202 is detected by the detecting means 204 and the focus of an image emitted from the exit end of the image transmitting means 201 and formed for the image receiving means 203 is adjusted by the focus adjusting means 205 on the basis of the image surface position of the image transmitting means 201 corresponding to the kind of the endoscope body 202.

The 14th embodiment of the present invention is shown in FIGS. 27 to 32.

Figures 26, 27:
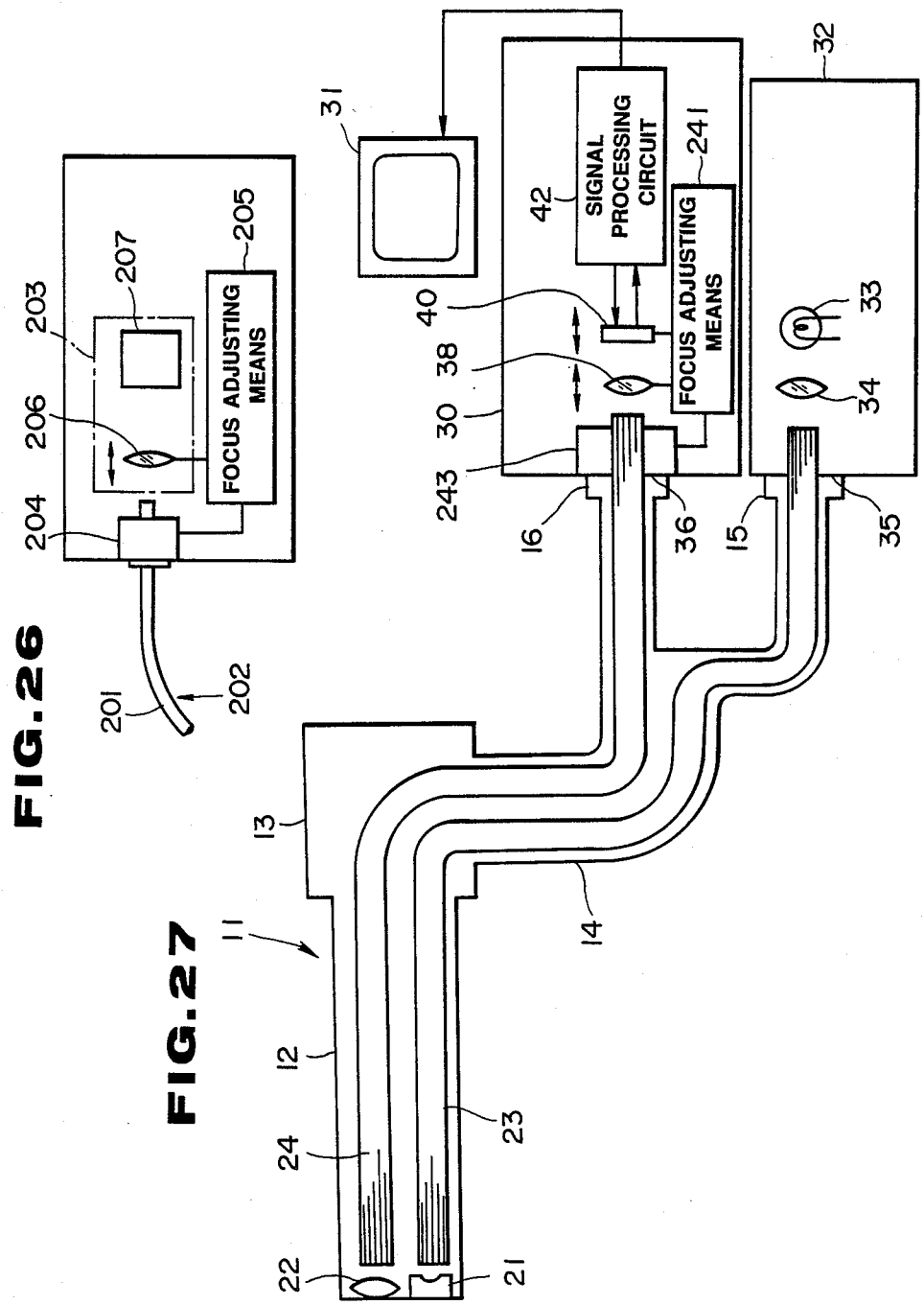
FIG. 26 is a conceptional view of the 14th and 15th embodiments.
FIGS. 27 to 32 relate to the 14th embodiment of the present invention.

As shown in FIG. 27, the endoscope apparatus comprises an endoscope 11, a video processor 30 and light source apparatus 32 connected with this endoscope 11 and a monitor 31 connected to the above mentioned video processor 30.

The above mentioned endoscope 11 comprises an elongate and, for example, flexible insertable part 12, a thick operating part 13 connected to this insertable part 12 at the rear end and a flexible universal cord 14 extended from the side of this operating part 13. The above mentioned universal cord 14 is branched on the tip side into two branches, one branch is provided at the tip with a light guide connector 15 and the other branch is provided at the end with an image guide connector 16. A light distributing lens 21 and an objective lens system 22 are arranged in the tip part of the above mentioned insertable part 12. The above mentioned light distributing lens 21 is provided on the rear end side with a light guide 23 consisting of a fiber bundle. This light guide 23 is inserted through the above mentioned insertable part 12, operating part 13 and universal cord 14 and is connected at the base end to a light guide connector 15. The tip surface of an image guide as an image transmitting means consisting of a fiber bundle is arranged in the image forming position of the above mentioned objective lens system 22. This image guide 24 is inserted through the above mentioned insertable part 12, operating part 13 and universal cord 14 and is connected at the exit end to an image guide connector 16.

On the other hand the above mentioned light source apparatus 32 is provided with a light guide connector receptacle 35 connected with the light guide connector 15 of the above mentioned endoscope 11. A lamp 33 is provided within this light source apparatus 32 and the light emitted from this lamp 33 is condensed by a condenser lens 34 and enters the light guide 23 entrance end of the light guide connector 15 connected to the above mentioned light guide connector receptacle 35.

The above mentioned video processor 30 is provided with an image guide connector receptacle 36 connected with the image guide connector 16 of the above mentioned endoscope 11. Within this video processor 30, an image forming lens 38 is arranged so as to be opposed to the image guide 24 exit end surface of the image guide connector 16 connected to the above mentioned image guide connector receptacle 36 and such solid state imaging device 40 as a CCD as an image receiving means is arranged in the image forming position of this image forming lens 38. A detecting means 243 detecting the kind of the endoscope 11 is provided near the above mentioned image guide connector receptacle 36 and the output of this detecting means 243 is input into a focus adjusting means 241 by which at least one of the above mentioned image forming lens 38 and solid state imaging device 40 is moved in the optical axial direction and is fixed in the optimum focal position on the basis of the image surface position of the image guide 24 corresponding to the kind of the endoscope detected by the above mentioned detecting means 43. A signal processing circuit 42 is connected to the above mentioned solid state imaging device 40 which is driven by the driving signal from a driving circuit within the above mentioned signal processing circuit 42. The signal read out is processed to be a video signal by the above mentioned signal processing circuit 42. The video signal from the above mentioned signal processing circuit 42 is input into a monitor 31 in which the endoscope image is displayed.

Figure 29:
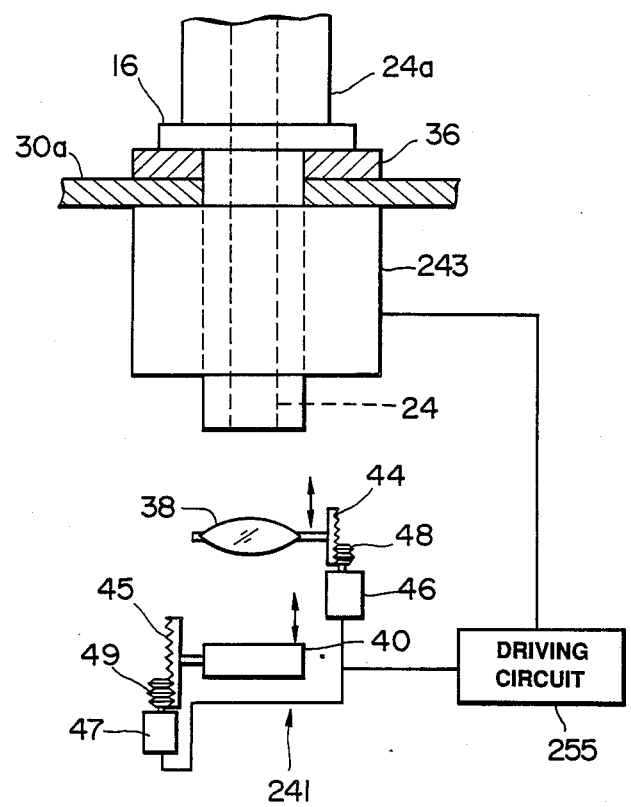

The above mentioned focus adjusting means 241 is formed as shown in FIG. 29.

An image guide connector 16 to which an image guide 24 is connected at the exit end is connected to an image guide connector receptacle 35 provided on a sheath 30a of a video processor 30. BY the way, the above mentioned image guide 24 is coated with an image guide sheath 24a.

An image forming lens 38 and solid state imaging device 40 arranged on the optical axis of the above mentioned image guide 24 are fitted respectively with racks 44 and 45 as moving means. Worms 48 and 49 fitted respectively to the driving shafts of motors 46 and 47 as driving apparatus are meshed respectively with the racks 44 and 45. By rotating the respective motors 46 and 47, the image forming lens 38 and solid state imaging device 40 can be moved in the optical axial direction.

The output signal of the detecting means 43 is input into a driving circuit 255. At least one of the image forming lens 38 and solid state imaging device 40 is moved in the optical axial direction on the basis of the output of this driving circuit 255 and the relative positions of the image forming lens 38 and solid state imaging device 40 are determined so as to make an in-focus state on the basis of the image surface position of the image guide 24.

Figure 28:
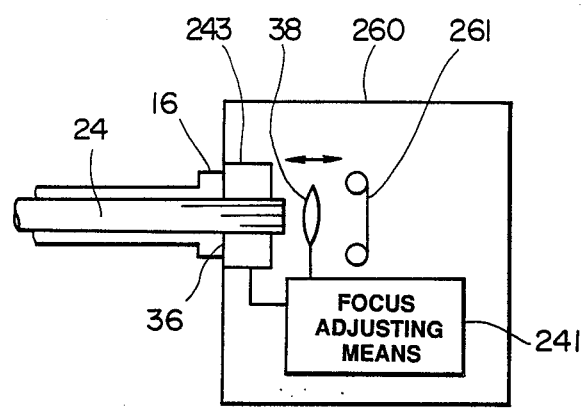

Also, in this embodiment, as a photographing means, instead of the above mentioned video processor 30 having the solid state imaging device 40, such still camera 260 as is shown in FIG. 28 can be connected to the endoscope 11.

The above mentioned still camera 260 comprises an image forming lens 38, a silver salt film 261 recording as a photograph the endoscope image formed by this image forming lens 38, a detecting means detecting the kind of the endoscope 11 and a focus adjusting means 241 forming the endoscope image on the above mentioned film 61 by moving the above mentioned image forming lens 38 in the optical axial direction on the basis of the output of this detecting means 243.

In this embodiment of such formation, the light emitted from the lamp 33 within the light source apparatus 32 enters the light guide 23 at the entrance end through the condenser lens 34, is emitted from the tip surface of this light guide 23 and is radiated to an object through a light distributing lens 21. The light returning from this object is made to form an image on the tip surface of the image guide 24 by the objective lens system 22. This object image is transmitted to the exit end surface of the above mentioned image guide 24. The image on the exit end surface of this image guide 24 is formed on the solid state imaging device 40 or silver salt film 261 by the image forming lens 38. The output signal of the above mentioned solid state imaging device 40 is processed to be a video signal by the signal processing circuit 42 and the video signal from this signal processing circuit 42 is input into the monitor 31 in which the endoscope image is displayed or the endoscope image is recorded as a photograph on the above mentioned silver salt film 261.

The kind of the endoscope 11 is detected by the detecting means 243 and, on the basis of the image surface position of the image guide 24 corresponding to the kind of the endoscope 11, by the focus adjusting means 241, the image forming lens 38 and solid state imaging device 40 are moved and the focus of the photographing means is moved to a predetermined position to obtain an in-focus state.

The above mentioned detecting means 241 shall be explained in the following with reference to FIGS. 30 to 32.

Figure 30:
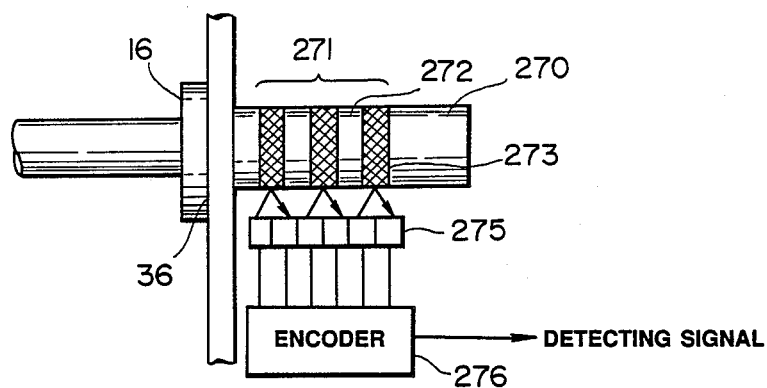

FIG. 30 shows a detecting means using a photoreflector.

In this example, a sensing band 271 having high reflection factor parts 272 and low reflection factor parts 273 is provided on the outer peripheral surface of an image guide mouthpiece 270 in the image guide connector 16 of the endoscope 11 connected to the image receiving means. A plurality of photoreflectors 275 are arranged in the positions opposed to this sensing band 271. The respective photoreflectors 275 emit lights, receive the returning lights reflected by the above mentioned sensing band and output signals corresponding to the reflection factors of the above mentioned sensing band 271. The outputs of the above mentioned photoreflectors 275 are input into an encoder 276 and are converted by this encoder 276 to a detecting signal which is output to a focus adjusting means 241.

When the above mentioned image guide mouthpiece 270 is inserted into the image guide connector receptacle 36 of the photographing means, signals will be output in response to the reflection factors of the sensing band 271 from the photoreflector 275. When the numbers and positions of the high reflection factor parts 272 and low reflection factor parts of the sensing band 271 are varied depending on the kind of the endoscope 11 or more particularly on the kind of the image surface position of the image guide 24, the outputs of the photoreflectors 275 will correspond to the kind of the image guide 24. When the outputs of these photoreflectors 275 are input into the encoder 276, a detecting signal showing the kind of the image surface position of the image guide 24 will be obtained.

Figure 31:
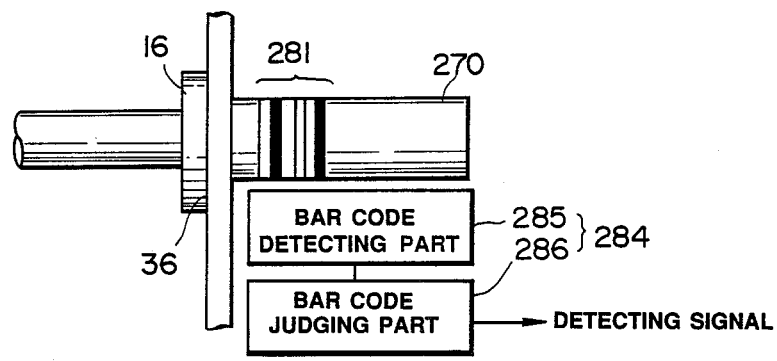

FIG. 31 shows a detecting means using bar codes.

In this example, bar codes 281 are formed on the outer peripheral surface of the image guide mouthpiece 27 of the endoscope 11 connected to the photographing means, are read by a bar code reader 284 having a bar code detecting part 285 detecting the bar codes 281 and a bar code judging part 286 judging the bar codes 281 from the output of this bar code detecting part 285 and are output as a detecting signal.

Figure 32:
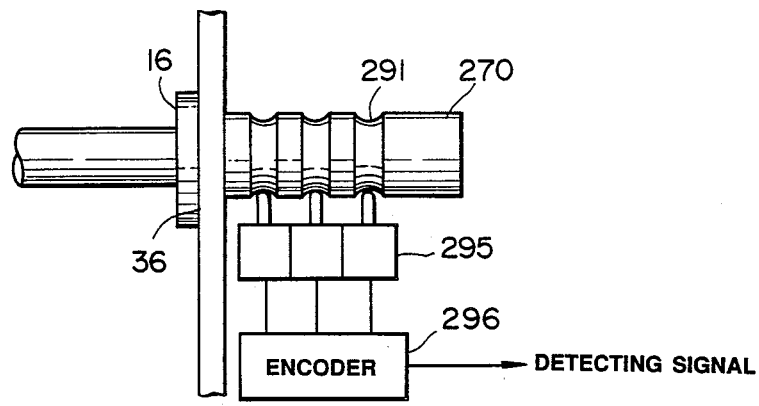

FIG. 32 shows a detecting means using microswitches.

In this example, a plurality of peripheral grooves 291 are provided on the outer periphery of the image guide mouthpiece 270 of the endoscope 11 connected to the image receiving means. A plurality of microswitches 295 are arranged so that their levers will be positioned respectively in the parts of the above mentioned grooves 291 when this image guide mouthpiece 270 is inserted into the image guide connector receptacle 36 of the image receiving means. Depending on the presence/absence of the above mentioned grooves 291, the respective microswitches 295 will be switched on/off and the on/off signals will be input into an encoder 296 and will be output as a detecting signal. Therefore, the kind of the endoscope 11 can be detected by the arrangement of the above mentioned grooves 291.

As explained above, according to this embodiment, the kind of the endoscope 11 is detected by the detecting means 43, the focus is adjusted by the focus adjusting means 241 on the basis of the image surface position of the image guide 24 corresponding to the kind of this endoscope 11 and therefore, irrespective of the kind of the endoscope 11, the endoscope image positively transmitted by the image guide 24 can be formed for the image receiving means and a focused image can be obtained.

Further, according to this embodiment, the focus can be easily adjusted at a high precision without requiring any minute manual adjustment and high mechanical precision.

Also, as shown in FIGS. 30 to 32, when the image guide mouthpiece 270 is simply marked, the kind of the endoscope 11 will be able to be easily detected.

Figure 33:
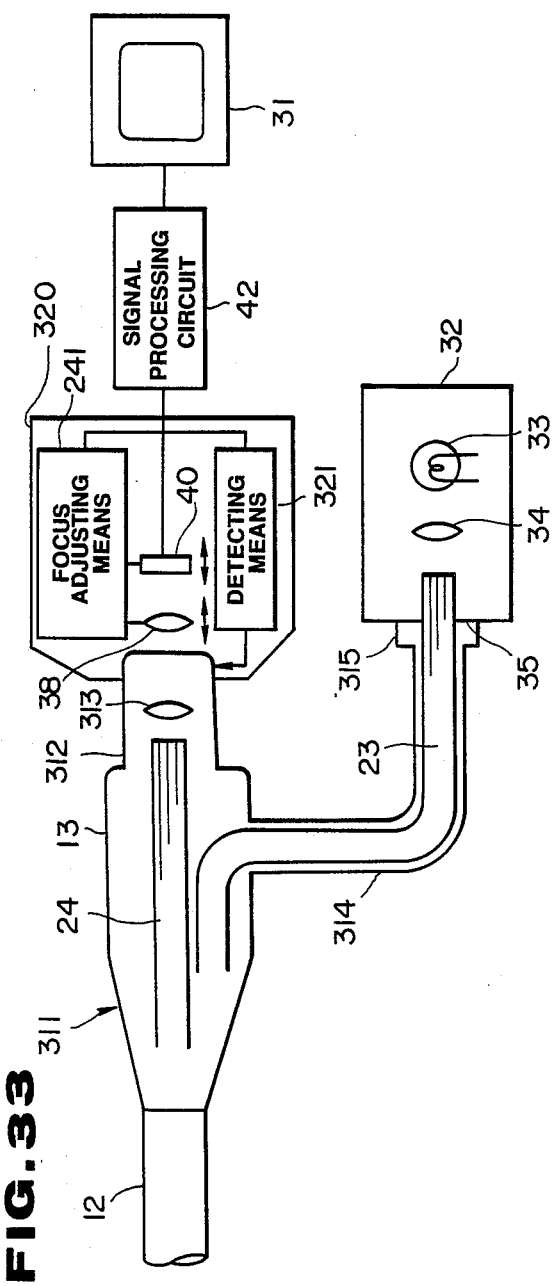
FIGS. 33 and 34 relate to the 15th embodiment of the present invention.
Figure 34:
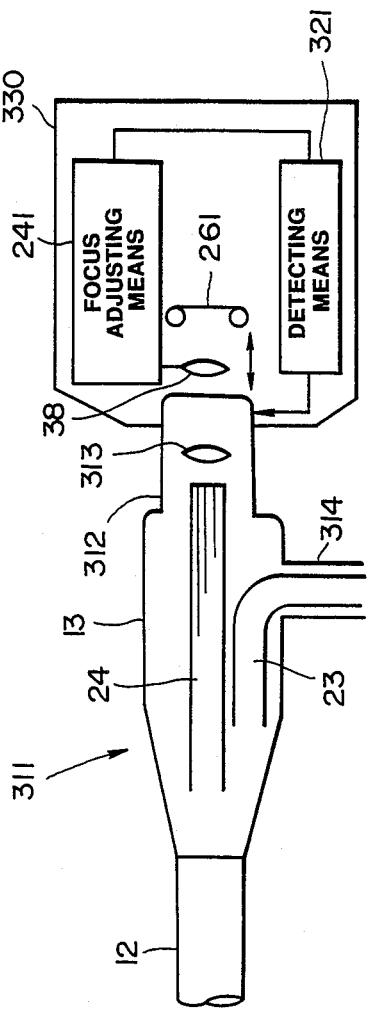
Figure 35:
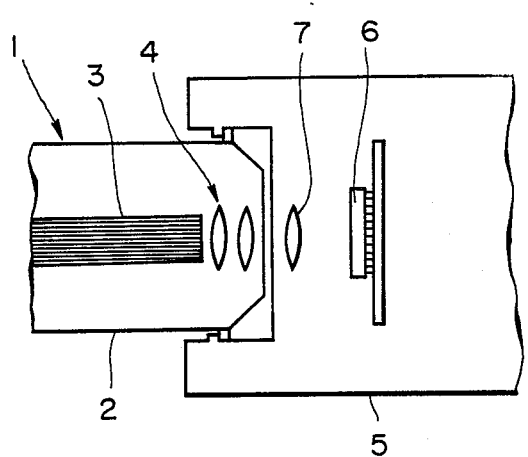
FIGS. 35 and 36 relate to related art examples.
Figure 36:
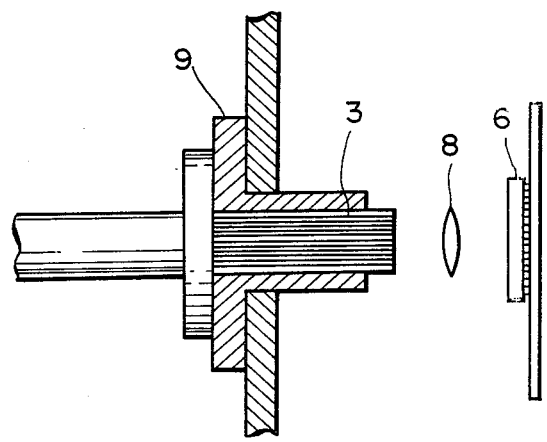

The 15th embodiment of the present invention is shown in FIGS. 33 and 34.

As shown in FIG. 33, the endoscope apparatus in this embodiment comprises an endoscope 311 whereby a naked eye observation is possible, a television camera 320 or such still camera 330 as is shown in FIG. 34 as a photographing means removably connected to the eyepiece part 312 of this endoscope 311, a signal processing circuit 42 connected to the above mentioned television camera 320 and a monitor 31 connected to the above mentioned signal processing circuit 42.

The above mentioned endoscope 311 comprises an elongate and, for example, flexible insertable part 12, a thick operating part 13 connected to this insertable part 12 at the rear end, the above mentioned eyepiece part 312 provided at the rear end of this operating part 13 and a flexible light guide cable extended from the side of the above mentioned operating part 13. The above mentioned light guide cable 314 is provided at the end with a light guide connector 315 connected to a light source apparatus 32.

The same as in the endoscope 11 shown in FIG. 27, a light distributing lens 21 and objective lens system 22 are arranged in the tip part of the above mentioned insertable part 12. A light guide 23 is provided on the rear end side of the above mentioned light distributing lens 21, is inserted through the above mentioned insertable part 12, operating part 13 and light guide cable 314 and is connected at the base end to a light guide connector 315.

The tip surface of an image guide 24 as an image transmitting means consisting of a fiber bundle is arranged in the image forming position of the above mentioned objective lens system 22. This image guide 24 is inserted through the above mentioned insertable part 12 and operating part 13 and is opposed at the exit end to an eyepiece lens 313 within the above mentioned eyepiece part 312. The object image formed by the above mentioned objective lens system 22 is transmitted to the eyepiece part 312 by the image guide 24 and can be observed with a naked eye from this eyepiece part 312.

As shown in FIG. 33, the above mentioned television camera 320 comprises a solid state imaging device 40 imaging an endoscope image and an image forming lens 38 forming the endoscope image on this solid state imaging device 40 and is provided with a focus adjusting means 41 focusing the endoscope image on the solid state imaging device 40 by moving in the optical axial direction at least one of the above mentioned image forming lens 38 and solid state imaging device 40 and a detecting means 321 detecting the kind of the above mentioned endoscope 311. The output of the above mentioned detecting means 321 is input into the focus adjusting means 41 by which, on the basis of the image surface position of the image guide 24 corresponding to the kind of the endoscope detected by the above mentioned detecting means 43, at least one of the above mentioned image forming lens 38 and solid state imaging device 40 is moved in the optical axial direction and is fixed in the optimum focal position.

On the other hand, the above mentioned still camera 330 comprises an image forming lens 38, a silver salt film 261 recording as a photograph an endoscope image formed by this image forming lens 38, a detecting means 321 detecting the kind of the endoscope 311 and a focus adjusting means 241 forming the endoscope image on the above mentioned film 261 by moving the above mentioned image forming lens 38 in the optical axial direction on the basis of the output of this detecting means 321.

In this embodiment, in case the television camera 320 is connected to the eyepiece part 312 of the endoscope 311, the endoscope image transmitted by the image guide 24 will be formed on the solid state imaging device 40 through the eyepiece lens 313 and image forming lens 38. The electric signal output from this solid state imaging device 40 is converted to a video signal by the signal processing circuit 42 and is input into a monitor 31. On the other hand, in case the still camera 330 is connected to the eyepiece part 312 of the endoscope 311, the endoscope image transmitted by the image guide 24 will be formed and recorded on the film 261 through the eyepiece lens 313 and image forming lens 38.

By the way, the above mentioned detecting means 321 can be formed the same as the detecting means 243 in the 14th embodiment. That is to say, the kind of the endoscope 311 can be detected by marking the eyepiece part 312 of the endoscope 311 as shown in FIGS. 30 to 32.

According to this embodiment, even in the television camera 320 or still camera 330 connected to the eyepiece part 312 of the endoscope 311, an accurate focused image can be obtained by detecting the kind of the endoscope 311.

The connection so far requiring a high precision of such photographing means as the television camera 320 or still camera 330 with the endoscope eyepiece part 312 becomes easy.

The other formations, operations and effects are the same as in the 14th embodiment.

By the way, in the 14th and 15th embodiments, the detecting means of the kind of the endoscope body is not limited to those shown therein but, by using the means disclosed, for example, in the publication of Japanese Patent Application Laid Open No. 2120/1986, a means of generating a discriminating signal by a plurality of voltage levels or the like may be provided on the endoscope body side and a means of responding to the above mentioned discriminating signal may be provided on the image receiving means side. Also, by using the means disclosed in the publication of Japanese Patent Application Laid Open No. 179129/1986, a memorizing part by an EEP or ROM memorizing the information of the kind may be provided on the endoscope body side and a means of reading out the information memorized in the above mentioned memorizing part may be provided on the image receiving means side. Further, by using the means disclosed in the publication of Japanese Patent Application Laid Open No. 84735/1987, a resistance corresponding to the kind may be provided on the endoscope body side and a means of detecting the voltage between the terminals of the resistance when a constant current is flowed to the above mentioned resistance may be provided on the image receiving means side. Also, by using the means disclosed in the publication of Japanese Patent Application Laid Open No. 271217/1988, a means of mechanically or electrically giving the information of discriminating the kind of the endoscope may be provided on the endoscope body side, a means of reading the above mentioned discriminating information may be provided on the image receiving means side, a data table of the image surface position of each endoscope body memorized by a ROM or the like in advance may be prepared on the image receiving means side and this data table may be checked with the above mentioned discriminating information to obtain the optimum focus adjusting information of each endoscope. The means of detecting the kind of the endoscope body is not limited to these.

The image transmitting means is not limited to the image guide consisting of a fiber bundle but a self-convergent photoconductor (Trade name: Selfox) or a relay lens may be also used.

The present invention is not limited to the automatic focus adjustment but includes manually adjusting the focus in response to the detected kind of the endoscope body.

As explained above, according to the 14th and 15th embodiments, a detecting means detecting the kind of the endoscope body and focus adjusting means whereby, on the basis of the image surface position of the image transmitting means corresponding to the kind of the endoscope body detected by this detecting means, the focus of the image emitted from the exit end of the image transmitting means and formed for the image receiving means can be adjusted are provided and therefore there is an effect that, irrespective of the kind of the endoscope, the endoscope image transmitted by the image transmitting means can be positively formed for the image receiving means.

What is claimed is:

1. An endoscope apparatus comprising:
an endoscope body having an elongate insertable part having an observing window in the tip part, an image forming optical system forming an object image by receiving a returning light from the object entering from said observing window and an image transmitting means inserted through said insertable part and transmitting the image formed by said image forming optical system to the rear end side of the insertable part;
an image receiving means removably connected with said endoscope body and receiving the image transmitted by said image transmitting means; and
a focus adjusting means provided in said image receiving means and capable of adjusting the focus of the image emitted from the exit end of said image transmitting means and formed for said photographing means.

2. An endoscope apparatus according to claim 1 further comprising a detecting means detecting a reference position on said endoscope body side to adjust the focus by said focus adjusting means.

3. An endoscope apparatus comprising:

an endoscope body having an elongate insertable part having an observing window in the tip part, an image forming optical system forming an object image by receiving a returning light from the object entering from said observing window and an image transmitting means inserted through said insertable part and transmitting the image formed by said image forming optical system to the rear end side of the insertable part;

an image receiving means removably connected with said endoscope body and receiving the image transmitted by said image transmitting means; and a focus adjusting means provided in said image receiving means and automatically adjusting the focus of the image emitted from the exit end of said image transmitting means and formed for said image receiving means with the reference position on said endoscope body side as a reference.

4. An endoscope apparatus comprising:

an endoscope body having an elongate insertable part having an observing window in the tip part, an image forming optical system forming an object image by receiving a returning light from the object entering from said observing window and an image transmitting means inserted through said insertable part and transmitting the image formed by said image forming optical system to the rear end side of the insertable part;

an image receiving means removably connected with said endoscope body and receiving the image transmitted by said image transmitting means;

a detecting means detecting a reference position on said endoscope body side; and a focus adjusting means provided in said image receiving means and automatically adjusting the focus of the image emitted from the exit end of said image transmitting means and formed for said image receiving means with the reference position detected by said detecting means as a reference.

5. An endoscope apparatus according to any one of claims 2 to 4 wherein the reference position on said endoscope body side is the exit end surface position of said image transmitting means.

6. An endoscope apparatus according to claim 1 further comprising a detecting means detecting the kind of said endoscope body to adjust the focus by said focus adjusting means, said focus adjusting means being capable of adjusting the focus on the basis of the image surface position of said image transmitting means corresponding to the kind of the endoscope body detected by said detecting means.

7. An endoscope apparatus comprising:

an endoscope body having an elongate insertable part having an observing window in the tip part, an image forming optical system forming an object image by receiving a returning light from the object entering from said observing window and an image transmitting means inserted through said insertable part and transmitting the image formed by said image forming optical system to the rear end side of the insertable part;

an image receiving means removably connected with said endoscope body and receiving the image transmitted by said image transmitting means:

a detecting means detecting the kind of said endoscope body; and a focus adjusting means provided in said image receiving means and automatically adjusting the focus of the image emitted from the exit end of said image transmitting means and formed for said image receiving means on the basis of the image surface position of said image transmitting means corresponding to the kind of the endoscope body detected by said detecting means.

8. An endoscope apparatus according to claim 2 or 4 wherein the reference position on said endoscope body side is the exit end surface position of said image transmitting means and said detecting means has a means of extracting the optical feature of the exit end surface of said image transmitting means and a means of comparing the size of the feature extracted by this extracting means.

9. An endoscope apparatus according to claim 8 wherein said image transmitting means consists of a fiber bundle and the optical feature of the exit end surface of said image transmitting means is a network pattern formed by the arrangement of respective fiber element lines of said fiber bundle.

10. An endoscope apparatus according to claim 2 or 4 wherein said detecting means has a means of optically measuring the reference position on said endoscope body side.

11. An endoscope apparatus according to claim 3 wherein said focus adjusting means has a means of mechanically positioning said image receiving means for the reference position on said endoscope body side.

12. An endoscope apparatus according to claim 10 wherein the reference position on said endoscope body side is the exit end surface position of said image transmitting means.

13. An endoscope apparatus according to claim 10 wherein the reference position on said endoscope body side is formed on the outer periphery of the exit end part of said image transmitting means.

14. An endoscope apparatus according to any one of claims 4, 6 and 7 wherein said image receiving means is a means photoelectrically converting an image.

15. An endoscope apparatus according to any one of claims 1 to 4, 6 and 7 wherein said image receiving means is a means of photographing an image.

16. An endoscope apparatus according to any one of claims 4, 6 and 7 wherein said endoscope body has within said insertable part an illuminating light transmitting means transmitting the illuminating light emitted from the tip of said insertable part.

17. An endoscope apparatus according to claim 16 further comprising a light source apparatus feeding an illuminating light to said illuminating light transmitting means, said image receiving means being provided within said light source apparatus.

18. An endoscope apparatus according to claim 14 further comprising a signal processing apparatus processing the signal for said image receiving means, said imaging receiving means being provided within said signal processing apparatus.

19. An endoscope apparatus according to any one of claims 4, 6 and 7 wherein said endoscope body has an eyepiece part whereby the image transmitted by said image transmitting means is made observable with a naked eye.

20. An endoscope apparatus according to claim 19 wherein said photographing means is removably connected to said eyepiece part.

21. An endoscope apparatus according to any one of claims 1 to 4 wherein said endoscope body has a removable eyepiece part whereby the image transmitted by said image transmitting means is made observable with a naked eye and said image receiving means is removably connected to said endoscope body by replacing said eyepiece part.

22. An endoscope apparatus according to any one of claims 4, 6 and 7 wherein said focus adjusting means has a means of moving said image receiving means in the optical axial direction.

23. An endoscope apparatus according to any one of claims 4, 6 and 7 wherein said focus adjusting means has a means of moving in the optical axial direction at least a part of the image forming optical system included in said image receiving means.

24. An endoscope image receiving apparatus removably connected with the endoscope body having an image transmitting means, comprising:
   an image receiving means receiving the image transmitted by said image transmitting means;
   a focus adjusting means capable of adjusting the focus of the image emitted from the exit end of said image transmitting means and formed for said image receiving means; and
   a detecting means detecting the reference position on said endoscope body side to adjust the focus by said focus adjusting means.

25. An endoscope image receiving apparatus removably connected with the endoscope body having an image transmitting means, comprising:
   an image receiving means receiving the image transmitted by said image transmitting means;
   a focus adjusting means whereby the focus of the image emitted from the exit end of said image transmitting means and formed for said image receiving means can be adjusted; and
   a focus adjusting means automatically adjusting the focus of the image emitted from the exit end of said image transmitting means and formed for said image receiving means with the reference position on said endoscope body side as a reference.

26. An endoscope image receiving apparatus removably connected with the endoscope body having an image transmitting means, comprising:
   an image receiving means receiving the image transmitted by said image transmitting means;
   a focus adjusting means whereby the focus of the image emitted from the exit end of said image transmitting means and formed for said image receiving means can be adjusted;
   a detecting means detecting the reference position on said endoscope body side; and
   a focus adjusting means automatically adjusting the focus of the image emitted from the exit end of said image transmitting means and formed for said image receiving means with the reference position detected by said detecting means as a reference.

27. An endoscope image receiving apparatus according to any one of claims 24 to 26 wherein the reference position on said endoscope body side is the exit end surface position of said image transmitting means.

28. An endoscope image receiving apparatus removably connected with the endoscope body having an image transmitting means, comprising:
   an image receiving means receiving the image transmitted by said image transmitting means;
   a focus adjusting means capable of adjusting the focus of the image emitted from the exit end of said image transmitting means and formed for said image receiving means; and
   a detecting means detecting the kind of said endoscope body to adjust the focus by said focus adjusting means,
   the focus adjustment being possible by said focus adjusting means on the basis of the image surface position of said image transmitting means corresponding to the kind of the endoscope body detected by said detecting means.

29. An endoscope image receiving apparatus removably connected with the endoscope body having an image transmitting means, comprising:
   an image receiving means receiving the image transmitted by said image transmitting means;
   a focus adjusting means capable of adjusting the focus of the image emitted from the exit end of said image transmitting means and formed for said image receiving means;
   a detecting means detecting the kind of said endoscope body; and
   a focus adjusting means automatically adjusting the focus of the image emitted from the exit end of said image transmitting means and formed for said image receiving means on the basis of the image surface position of said image transmitting means corresponding to the kind of the endoscope body detected by said detecting means.

30. An endoscope image receiving apparatus according to claim 24 or 26 wherein the reference position on said endoscope body side is the exit end surface position of said image transmitting means and said detecting means has a means of extracting the optical feature of the exit end surface of said image transmitting means and a means of comparing the size of the feature extracted by said extracting means.

31. An endoscope image receiving apparatus according to claim 30 wherein said image transmitting means consists of a fiber bundle and the optical feature of the exit end surface of said image transmitting means is a network pattern formed by the arrangement of respective fiber element lines of said fiber bundle.

32. An endoscope image receiving apparatus according to claim 24 or 26 wherein said detecting means has a means of optically measuring the reference position on said endoscope body side.

33. An endoscope image receiving apparatus according to claim 25 wherein said focus adjusting means has a means of mechanically positioning said image receiving means for the reference position on said endoscope body side.

34. An endoscope image receiving apparatus according to claim 32 wherein the reference position on said endoscope body side is the exit end surface position of said image transmitting means.

35. An endoscope image receiving apparatus according to claim 32 wherein the reference position on said endoscope body side is formed on the outer periphery of the exit end part of said image transmitting means.

36. An endoscope image receiving apparatus according to any one of claims 24 to 26, 28 and 29 wherein said image receiving means is a means photoelectrically converting an image.

37. An endoscope image receiving apparatus according to any one of claims 24 to 26, 28 and 29 wherein said image receiving means is a means of photographing an image.

38. An endoscope image receiving apparatus according to any one of claims 24 to 26, 28 and 29 wherein said endoscope body has an eyepiece part making the image transmitted by said image transmitting means observable with a naked eye and said endoscope image receiving apparatus is removably connected to said eyepiece part.

39. An endoscope image receiving apparatus according to any one of claims 24 to 26 wherein said endoscope body has a removably fitted eyepiece part making the image transmitted by said image transmitting means observable with a naked eye and said endoscope image receiving apparatus is removably connected to said endoscope body by replacing said eyepiece part.

40. An endoscope image receiving apparatus according to any one of claims 24 to 26, 28 and 29 wherein said focus adjusting means has a means moving said image receiving means in the optical axial direction.

41. An endoscope image receiving apparatus according to any one of claims 24 to 26, 28 and 29 wherein said focus adjusting means has a means moving in the optical axial direction at least a part of the image forming optical system included in said endoscope image receiving apparatus.

* * * * *